(12) United States Patent
Salomon et al.

(10) Patent No.: US 8,822,172 B2
(45) Date of Patent: Sep. 2, 2014

(54) METHOD OF DETECTING ISOLEVUGLANDIN PHOSPHOLIPID ADDUCTS

(75) Inventors: Robert Salomon, Mayfield Village, OH (US); Wei Li, College Station, TX (US)

(73) Assignee: Case Western Reserve University, Cleveland, OH (US)

( * ) Notice: Subject to any disclaimer, the term of this patent is extended or adjusted under 35 U.S.C. 154(b) by 846 days.

(21) Appl. No.: 12/692,692

(22) Filed: Jan. 25, 2010

(65) Prior Publication Data

US 2011/0027815 A1     Feb. 3, 2011

Related U.S. Application Data

(60) Provisional application No. 61/146,815, filed on Jan. 23, 2009, provisional application No. 61/147,632, filed on Jan. 27, 2009.

(51) Int. Cl.
*C12Q 1/34* (2006.01)

(52) U.S. Cl.
USPC ................................. 435/18; 435/4

(58) Field of Classification Search
None
See application file for complete search history.

(56) References Cited

U.S. PATENT DOCUMENTS

| | | | |
|---|---|---|---|
| 5,686,250 A | 11/1997 | Salomon | |
| 7,172,874 B2 | 2/2007 | Hollyfield et al. | |
| 7,341,839 B2 | 3/2008 | Hollyfield et al. | |
| 7,604,948 B2 | 10/2009 | Amaral et al. | |
| 7,632,685 B2 | 12/2009 | Ivey et al. | |
| 7,645,613 B2 | 1/2010 | Ivey et al. | |
| 2009/0093009 A1 | 4/2009 | Chan et al. | |
| 2009/0253156 A1 | 10/2009 | Patton et al. | |

OTHER PUBLICATIONS

Davies S.S. et al., Measurement of chronic oxidative and inflammatory stress by quantification of isoketal/levuglandin c-ketoaldehyde protein adducts using liquid chromatography tandem mass spectrometry, Nature Protocols, 2007, vol. 2, No. 9, pp. 2079-2091.*
Kawai Y. et al., Formation of N(epsilon)-(succinyl)lysine in vivo: a novel marker for docosahexaenoic acid-derived protein modification, Journal of Lipid Research, 2006, vol. 47, pp. 1386-1398.*
Bernoud-Hubac N. et al., Formation of Highly Reactive gamma-Ketoaldehydes (Neuroketals) as Products of the Neuroprostane Pathway, The Journal of Biological Chemistry, 2001, vol. 276, No. 33, pp. 30964-30970.*
Brame C.J. et al., Modification of Proteins by Isoketal-containing Oxidized Phospholipids, The Journal of Biological Chemistry, Apr. 2, 2004, vol. 279, No. 14, pp. 13447-13451.*
Salomon, Robert G., et al., "Isolevuglandin-protein Adducts in Oxidized Low Density Lipoprotein and Human Plasma: A strong Connection with Cardiovascular Disease", TCM vol. 10, No. 2, 2000.
Salomon, Robert G., et al., "Isolevuglandin-protein adducts in humans: products of free radical-induced lipid oxidation through the isoprostane pathway", Biochimica et Biophysica Acta 1485 (2000) 225-235.
Salomon, Robert G., "Levuglandins and Isolevuglandins: Stealthy Toxins of Oxidative Injury", Antioxidants & Redox Signaling vol. 7, Nos. 1 & 2, 2005.
Talati, Megha, et al., "Oxidant stress modulates murine allergic airway responses", Free Radical Biology & Medicine 40 (2006) 1210-1219.
Zagol-Ikapitte, Irene, et al., "Prostaglandin $H_2$-derived adducts of proteins correlated with Alzheimer's disease severity", Journal of Neurochemistry, 2005, 94, 1140-1145.
Bernoud-Hubac, Nathalie, et al., "Covalent Binding of Isoketals to Ethanolamine Phospholipids", Free Radical Biology & Medicine, vol. 37, No. 10, pp. 1604-1611, 2004.
Davies, Sean S. et al., "Localization of Isoketal Adducts In Vivo Using A Single-Chain Antibody", Free Radical Biology & Medicine, vol. 36, No. 9, pp. 1163-1174, 2004.
Davies, Sean S. et al., "Isoketals: highly reactive γ-ketoaldehydes formed from the $H_2$-isoprostane pathway", Chemistry and Physics of Lipids 128 (2004) 85-99.
Fukuda, Koji, et al., "Oxidative Mediated Lipid Peroxidation Recapitulates Proarrhythmic Effects on Cardiac Sodium Channels", *Circ. Res.* 2005;97;1262-1269, Originally Published online Nov. 10, 2005.
Govindarajan, Bharathi et al., "Isolevuglandin-Modified Proteins, Including Elevated Levels of Inactive Calpain-1, Accumulate in Glaucomatous Trabecular Meshwork", Biochemistry 2008, 47, 817-825.
Li, Wei et al., "Isolevuglandin covalently modify phospatidylethanolamines in vivo: Detection and quantitative analysis of hydroxylactam adducts", free Radical Biology & Medicine 47 (2009) 1539-1552.
Lu, Liang et al., "Serum Vitamin E and Oxidative Protein Modification in Hemodialysis: A Randomized Clinical Trial", Am J. Kidney Dis 50:305-313, Aug. 2007.
Salomon, Robert G., et al., "Levuglandin $E_2$-Protein Adducts in Human Plasma and Vasculature", Chem. Res. Toxicol. 1997, 10, 536-545.

* cited by examiner

*Primary Examiner* — Satyendra Singh
(74) *Attorney, Agent, or Firm* — Tarolli, Sundheim, Covell & Tummino LLP

(57) ABSTRACT

A method of measuring isolevuglandin and/or levuglandin adducts associated with oxidative injury in a subject includes obtaining a bodily sample from a subject suspected of including isolevuglandin and/or levuglandin phospholipid adducts, hydrolyzing isolevuglandin and/or levuglandin phospholipid adducts from the sample with an enzyme that forms isolevuglandin and/or levuglandin phospholipid derivatives, and determining the amount of isolevuglandin and/or levuglandin phospholipid derivatives by mass spectrometry.

24 Claims, 23 Drawing Sheets

METHOD OF DETECTING ISOLEVUGLANDIN PHOSPHOLIPID ADDUCTS

RELATED APPLICATION

This application claims priority from U.S. Provisional Application No. 61/146,815, filed Jan. 23, 2009, and 61/147,632, filed Jan. 27, 2009, the subject matter, which is incorporated herein by reference.

TECHNICAL FIELD

The present invention relates to a method of measuring isolevuglandin (and/or levuglandin) adducts in a subject associated with oxidative damage and particularly relates to a method of measuring oxidative damage in a tissue or a subject my measuring the level of isolevuglandin (and/or levuglandin) adducts.

BACKGROUND OF THE INVENTION

Levuglandins (LGs) and isolevuglandins (isoLGs) are a family of reactive oxidized lipids formed by rearrangement of endoperoxide intermediates generated, respectively, through the cyclooxygenase and free radical-induced cyclooxygenation of arachidonates.

The $\gamma$-ketoaldehyde functionality of the LGs makes them extraordinarily reactive towards primary amino groups in biolomolecules. LGs and isoLGs react with the $\epsilon$-amino groups of lysyl residues in proteins to produces covalent adducts with greater avidity than most other lipid oxidation products, e.g., 4-hydroxynonenal (4-HNE) or malondialdehyde (MDA). This feature makes covalent LG/isoLG adducts attractive as biomarkers to evaluate the oxidative injury in the tissues. LGs/isoLGs initially react with the primary amino groups to form Schiff base adducts in seconds, which are transformed to pyrrole adducts in minutes. However, these highly alkylated pyrroles are chemically sensitive compounds in the presence of oxygen and are further oxidized in a few hours to stable end products, lactams and hydroxylactams (HLs). IsoLGE$_2$-protein, iso[4]LGE$_2$-protein and iso[7]LGD$_2$-protein adducts are generated upon oxidation of LDL in vitro. Formation of isoLG protein adducts in vivo has also been confirmed by a variety of immunological and mass spectrometric methods. The levels of isoLG-protein adducts were elevated in diseases associated with oxidative injury.

SUMMARY OF THE INVENTION

The present invention relates to a method of measuring isolevuglandin and/or levuglandin adducts associated with oxidative injury in a subject. The method includes obtaining a bodily sample from a subject suspected of including isolevuglandin and/or levuglandin phospholipid adducts. Isolevuglandin and/or levuglandin phospholipid adducts from the sample are then hydrolyzed with an enzyme that forms isolevuglandin and/or levuglandin phospholipid derivatives. The amount of isolevuglandin and/or levuglandin phospholipid derivatives is then determined by mass spectrometry. The amount of isolevuglandin and/or levuglandin phospholipid derivatives is determinative of the level of isolevuglandin and/or levuglandin phospholipid adducts in the sample and indicative of the level of oxidative injury in the subject.

In an aspect of the invention, the isolevuglandin and/or levuglandin phospholipid adducts are extracted from the bodily sample prior to hydrolysis with the enzyme. The isolevuglandin and/or levuglandin phospholipid adducts can be extracted from the bodily sample in the presence of at least one of a chelating agent or antioxidant to inhibit oxidation of the bodily sample. The chelating agent or antioxidant can include at least one of ethylenediaminetetraacetic acid (EDTA) or butylated hydroxytoluene (BHT).

In another aspect of the invention, the bodily sample can include at least one of blood, plasma, sera, saliva, mucous, synovial fluid, cerebrospinal fluid, urine, stool, cells, a cellular extract, a tissue sample, or a tissue biopsy. In one example, the bodily sample can include liver tissue, and the method can be used to measure ethanol induced oxidative liver injury in a subject.

In a further aspect of the invention, the enzyme can include a phospholipase, such as phospholipase A, B, C, or D. By way of example, the enzyme can be phospholipase $A_2$.

In another aspect of the invention, an increased level of isolevuglandin and/or levuglandin phospholipid adducts in the subject compared to a control level is indicative of an increased level of oxidative injury in the subject. In one example, the control level includes a level of isolevuglandin and/or levuglandin phospholipid adducts in a normal or healthy subject or tissue. In another example, the control level can include a previously measured level of isolevuglandin and/or levuglandin phospholipid adducts in the subject or tissue of the subject.

The present invention also relates to a method of measuring oxidative damage in a subject. The method includes obtaining a bodily sample suspected of including isolevuglandin and/or levuglandin phospholipid adducts from a subject. Lipids are extracted from the biological sample in the presence of a chelating agent or antioxidant. Isolevuglandin and/or levuglandin phospholipid adducts from the extracted are hydrolyzed with phospholipase A2 to form isolevuglandin and/or levuglandin phospholipid derivatives. The amount of isolevuglandin and/or levuglandin phospholipid derivatives is then determined by mass spectrometry. The amount of isolevuglandin and/or levuglandin phospholipid derivatives is determinative of the level of isolevuglandin and/or levuglandin phospholipid adducts in the sample and indicative of the level of oxidative damage in the subject.

In an aspect of the invention, the chelating agent or antioxidant can include at least one of ethylenediaminetetraacetic acid (EDTA) or butylated hydroxytoluene (BHT).

In another aspect of the invention, the bodily sample can include at least one of blood, plasma, sera, saliva, mucous, synovial fluid, cerebrospinal fluid, urine, stool, cells, a cellular extract, a tissue sample, or a tissue biopsy. In one example, the bodily sample can include liver tissue and the method can be used to measure ethanol induced oxidative liver injury in a subject.

In a further aspect of the invention, the enzyme can include a phospholipase, such as phospholipase A, B, C, or D. By way of example, the enzyme can be phospholipase $A_2$.

In another aspect of the invention, an increased level of isolevuglandin and/or levuglandin phospholipid adducts in the subject compared to a control level is indicative of an increased level of oxidative injury in the subject. In one example, the control level includes a level of isolevuglandin and/or levuglandin phospholipid adducts in a normal or healthy subject or tissue. In another example, the control level can include a previously measured level of isolevuglandin and/or levuglandin phospholipid adducts in the subject or tissue of the subject.

DETAILED DESCRIPTION

Figure 1:
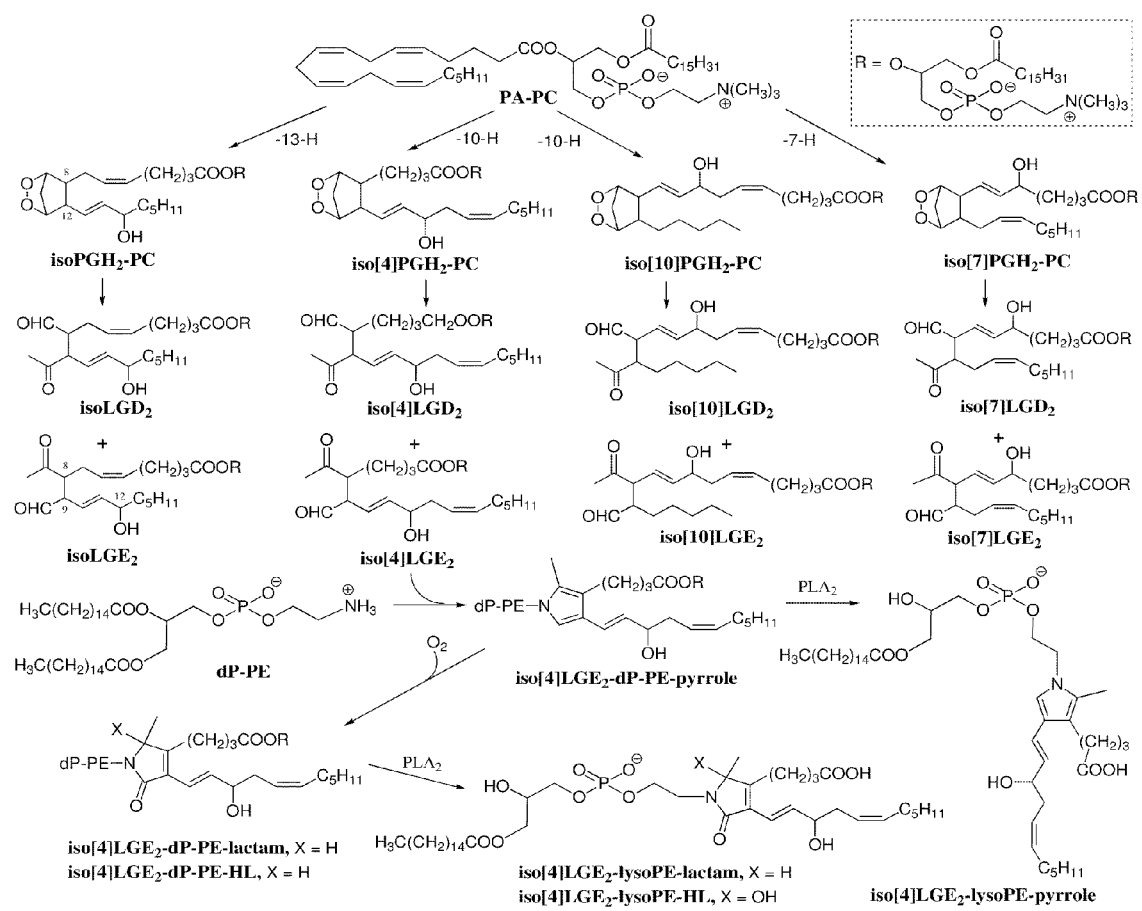
FIG. 1 is a schematic diagram illustrating free radical induced cyclooxygenation of PA-PC is postulated to generated a family of eight structurally isoLG stereoisomers through isoprostanoid endoperoxide intermediates. Hydroxylactam end products are generated by the reaction of isoLGs with 2-lysoPE.

The present invention relates to a method of measuring isolevuglandin (isoLG) (and/or levuglandin (LG)) adducts associated with oxidative damage in a subject and particularly relates to a method of measuring oxidative damage in a tissue or a subject by measuring the level of isolevuglandin (and/or levuglandin) adducts. The levels of isoLG and LG adducts are elevated in diseases and pathologies associated with oxidative damage or injury. For example, increased levels of isoLG adducts and LG adducts have been observed in vivo during a wide variety of conditions associated with inflammation and oxidative stress including atherosclerosis, end stage kidney disease, myocardial infarction, glaucoma, hyperoxia, allergic inflammation, sepsis, macular degeneration, and liver injury.

The involvement of LGs and isoLGs has also been suggested for other pathologies including: platelet activation (Boutaud et al., Levuglandinyl adducts of proteins are formed via a prostaglandin H2 synthase-dependent pathway after platelet activation, The Journal of biological chemistry 278 (2003) 16926-16928), Alzheimer's disease (Boutaud et al., PGH2-derived levuglandin adducts increase the neurotoxicity of amyloid beta1-42, Journal of neurochemistry 96 (2006) 917-923.3; Boutaud et al., Prostaglandin H2 (PGH2) accelerates formation of amyloid beta1-42 oligomers, Journal of neurochemistry 82 (2002) 1003-1006; Zagol-Ikapitte et al., Prostaglandin H(2)-derived adducts of proteins correlate with Alzheimer's disease severity, Journal of neurochemistry 94 (2005) 1140-1145), cardiac malfunction, e.g. arrythmias (Brame et al., 2nd, Modification of proteins by isoketal-containing oxidized phospholipids, The Journal of biological chemistry 279 (2004) 13447-13451; Fukuda et al., 2nd, J. R. Balser, Oxidative mediated lipid peroxidation recapitulates proarrhythmic effects on cardiac sodium channels, Circulation research 97 (2005) 1262-1269.), oxidative stress in the bronchia, e.g., associated with asthma (Davies et al., Localization of isoketal adducts in vivo using a single-chain antibody, Free radical biology & medicine 36 (2004) 1163-1174; Talati et al., 2nd, J. R. Sheller, Oxidant stress modulates murine allergic airway responses, Free radical biology & medicine 40 (2006) 1210-1219), glaucoma (Govindarajan et al., Isolevuglandin-modified proteins, including elevated levels of inactive calpain-1, accumulate in glaucomatous trabecular meshwork, Biochemistry 47 (2008) 817-825; Govindarajan, Neuroprotection in glaucoma using calpain-1 inhibitors: regional differences in calpain-1 activity in the trabecular meshwork, optic nerve and implications for therapeutics, CNS & neurological disorders drug targets 7 (2008) 295-304), kidney disease (Lu et al., Serum vitamin E and oxidative protein modification in hemodialysis: a randomized clinical trial, Am J Kidney Dis 50 (2007) 305-313; Salomon et al., Levuglandin E2-protein adducts in human plasma and vasculature, Chemical research in toxicology 10 (1997) 536-545; R. G. Salomon, E. Batyreva, K. Kaur, D. L. Sprecher, M. J. Schreiber, J. W. Crabb, M. S. Penn, A. M. DiCorletoe, S. L. Hazen, E. A. Podrez, Isolevuglandin-protein adducts in humans: products of free radical-induced lipid oxidation through the isoprostane pathway, Biochimica et biophysica acta 1485 (2000) 225-235), DNA dysfunction associated with oxidative stress or cyclooxygenase activity (K. K. Murthi, L. R. Friedman, N. L. Oleinick, R. G. Salomon, Formation of DNA-protein cross-links in mammalian cells by levuglandin E2, Biochemistry 32 (1993) 4090-4097), retinal degeneration (K. P. Ng, B. Gugiu, K. Renganathan, M. W. Davies, X. Gu, J. S. Crabb, S. R. Kim, M. B. Rozanowska, V. L. Bonilha, M. E. Rayborn, R. G. Salomon, J. R. Sparrow, M. E. Boulton, J. G. Hollyfield, J. W. Crabb, Retinal pigment epithelium lipofuscin proteomics, Mol Cell Proteomics 7 (2008) 1397-1405), cardiovascular disease (R. G. Salomon, G. Subbanagounder, J. O'Neil, K. Kaur, M. A. Smith, H. F. Hoff, G. Perry, V. M. Monnier, Levuglandin E2-protein adducts in human plasma and vasculature, Chemical research in toxicology 10 (1997)

536-545; R. G. Salomon, E. Batyreva, K. Kaur, D. L. Sprecher, M. J. Schreiber, J. W. Crabb, M. S. Penn, A. M. DiCorletoe, S. L. Hazen, E. A. Podrez, Isolevuglandin-protein adducts in humans: products of free radical-induced lipid oxidation through the isoprostane pathway, Biochimica et biophysica acta 1485 (2000) 225-235), oxidative brain injury, e.g., from stroke (J. W. Schmidley, J. Dadson, R. S. Iyer, R. G. Salomon, Brain tissue injury and blood-brain barrier opening induced by injection of LGE2 or PGE2, Prostaglandins, leukotrienes, and essential fatty acids 47 (1992) 105-110), faulty mitosis (K. K. Murthi, R. G. Salomon, H. Sternlicht, Levuglandin E2 inhibits mitosis and microtubule assembly, Prostaglandins 39 (1990) 611-622.), chronic inflammatory diseases and infection (E. Poliakov, M. L. Brennan, J. Macpherson, R. Zhang, W. Sha, L. Narine, R. G. Salomon, S. L. Hazen, Isolevuglandins, a novel class of isoprostenoid derivatives, function as integrated sensors of oxidant stress and are generated by myeloperoxidase in vivo, Faseb J 17 (2003) 2209-2220.). (S. S. Davies, V. Amarnath, C. J. Brame, O. Boutaud, L. J. Roberts, 2nd, Measurement of chronic oxidative and inflammatory stress by quantification of isoketal/levuglandin gamma-ketoaldehyde protein adducts using liquid chromatography tandem mass spectrometry, Nature protocols 2 (2007) 2079-2091; R. G. Salomon, Levuglandins and isolevuglandins: stealthy toxins of oxidative injury, Antioxidants & redox signaling 7 (2005) 185-201; R. G. Salomon, K. Kaur, E. Batyreva, Isolevuglandin-protein adducts in oxidized low density lipoprotein and human plasma: a strong connection with cardiovascular disease, Trends in cardiovascular medicine 10 (2000) 53-59).

The level of IsoLG and LG adducts, such as iso[4]LGE$_2$ phosphatidylethanolamine (PE) hydrolactams (iso[4]LGE$_2$-PE-HLs), in biological samples of subjects with oxidative injury have previously not been detectable (and/or quantifiable) by mass spectrometry because such adducts present as a complex mixture in which the levels of individual species are not sufficient for detection. It was found that mixtures of isoLG adducts can be simplified by selective hydrolysis to form isoLG phospholipid derivatives that can be detected and quantified by mass spectrometry. Detection and quantification of isoLG derivatives can be used determine the levels of phosphatidylethanolamine adducts of isolevuglandins and levuglandin in bodily samples (e.g., blood, cerebrospinal fluid, synovial fluid, tissue). The detected levels of phosphatidylethanolamine adducts of isolevuglandins can be correlated with oxidative damage in the subject and used to detect and/or measure oxidative injury or damage associated for example with physiological abnormalities or pathologies including, for example, cardiovascular disease, macular degeneration, and liver injury.

In one embodiment of the invention, a method of measuring isolevuglandin (isoLG) (and/or levuglandin (LG)) adducts associated with oxidative damage in a subject includes obtaining a bodily sample from a subject that is suspected of having or at risk of an oxidative injury or oxidative damage. The subject can include an animal, such as a mammal including a small mammal (e.g., mouse, rat, rabbit, or cat) or a larger mammal (e.g., dog, pig, or human). In one example, the subject is a large mammal, such as a human, that is suspected of having or at risk of oxidative injury or damage.

The bodily sample can include any bodily sample that is suspected of including isoLG or LG phospholipid adducts associated with oxidative injury or damage. By associated with oxidative injury or damage it is meant the isoLG or LH phospholipid adducts result from or contribute to the pathogenesis of the oxidative injury or damage.

The bodily sample can be obtained either invasively or non-invasively from the subject but is preferably obtained non-invasively. The bodily sample obtained from the subject can potentially include body fluids, such as blood, plasma, serum, urine, blood, fecal matter, cerebrospinal fluid (CSF), semen, saliva, mucous, and cell extract as well as solid tissue, such as cells, a tissue sample, or a tissue biopsy. It will be appreciated by one skilled in the art that other bodily samples not listed can also be used in accordance with the present invention. In accordance with an aspect of the present invention, the bodily sample can comprise blood sample that can be obtained non-invasively from the subject.

The bodily samples can be obtained from the subject using sampling devices such as swabs, syringes, or other sampling devices used to obtain liquid and/or solid bodily samples either invasively (i.e., directly from the subject) or non-invasively. These samples can then be stored in storage containers. The storage containers used to contain the collected sample can comprise a non-surface reactive material, such as polypropylene. The storage containers should generally not be made from untreated glass or other sample reactive material to prevent the sample from becoming absorbed or adsorbed by surfaces of the glass container.

Collected samples stored in the container may be stored under refrigeration temperature. For longer storage times, it is desirable that the collected sample be frozen to retard decomposition and facilitate storage. For example, samples obtained from the subject can be stored in a falcon tube and cooled to a temperature of about −70° C. Advantageously, the collected bodily sample can be stored in the presence of a chelating agent, such as ethylenediaminetetraacetic acid (EDTA), and/or an antioxidant, such as butylated hydroxytoluene (BHT), to inhibit oxidation of the sample.

Bodily samples obtained from the subject can then extracted with a solvent, such as an organic solvent, to isolate and/or separate lipids including LG and/or isolG phospholipid adducts from the bodily sample. In one aspect of the invention, the lipids can be extracted or separated from the bodily sample by contacting the bodily sample with at least one organic solvent under conditions such that an extracted sample is produced. The solvent can include any chemical useful for the removal (i.e., extraction) of a lipid from a bodily sample. For example, where the bodily sample comprises plasma, the solvent can include a chloroform/methanol mixture (e.g., 1/2 v/v). It will be appreciated by one skilled in the art that the solvent is not strictly limited to this context, as the solvent may be used for the removal of lipids from a liquid mixture, with which the liquid is immiscible in the solvent. Those skilled in the art will further understand and appreciate other appropriate solvents that can be employed to extract lipids from the bodily sample.

The solvent can include solvent mixtures comprising miscible, partially miscible, and/or immiscible solvents. For example, the solvent can comprise a mixture of chloroform and methanol. The solvent can also be combined with other solvents or liquids, which are not useful for the removal of the lipids. The other solvents in the solvent mixture can act as carriers, which facilitate mixing of the solvent with the bodily sample or transfer of the extracted lipids from the bodily sample.

In another aspect of the invention, the bodily sample can be extracted in the presence of a chelating agent, such as ethylenediaminetetraacetic acid (EDTA), and/or an antioxidant, such as butylated hydroxytoluene (BHT), to inhibit oxidation of the sample and extracted lipid.

Following extraction of the lipids from the bodily sample, LG and/or isoLG phospholipid adducts in the extract are hydrolyzed with an enzyme that forms isolevuglandin and/or levuglandin phospholipid derivatives that are capable of being readily detected and quantified by mass spectrometry. In one aspect of the invention, the enzyme can include a phospholipase that hydrolyzes phospholipids, such as phosphatidylethanolamine, of the LG and/or isoIG phospholipid adducts, such as isoLG-diacyl-PE, to isolevuglandin and/or levuglandin phospholipid derivatives that are capable of being readily detected and quantified by mass spectrometry. Examples of phospholipases that can be used in accordance with the method of the present invention include phospholipase $A_1$, $A_2$, B, C, and/or D. Phospholipase $A_1$ selectively cleaves the SN-1 acyl chain of the phospholipid of an isoLG phospholipid adduct. Phospholipase $A_2$ selectively cleaves the SN-2 acyl chain of the phospholipid of an isoLG phospholipid adduct. Phospholipase B selectively cleaves both the SN-1 and SN-2 acyl chains of the phospholipid of an isoLG phospholipid adduct. Phospholipase C selectively cleaves the phospholipid of an isoLG phospholipid adduct before the phosphate, releasing diacylglycerol and a phosphate-containing head group. Phospholipase D selectively cleaves the phospholipid of an isoLG phospholipid adduct after the phosphate, releasing phosphatidic acid and an alcohol.

In one example of the invention, phospholipase $A_2$ in the presence of $CaCl_2$ is used to catalyze hydrolysis of isoLG-diacyl-PE precursors in the lipid extracts to isoLG-lysoPE-HL derivatives that can be readily detected and quantified by mass spectrometry. In another example of the invention, phospholipase D is used to catalyze hydrolysis of isoLG-diacyl-PE precursors in the lipid extracts to isoLG derivatives that can be readily detected and quantified by mass spectrometry.

In another aspect of the invention, the enzyme can include a carboxylic ester hydrolase that is related to phospholipase. One example of a carboxylic ester hydrolase that can be used to hydrolyzed with an enzyme that forms isolevuglandin and/or levuglandin phospholipid adducts to isolevuglandin and/or levuglandin phospholipid derivatives is platelet activating factor (PAF) acetylhydrolase. It will be appreciate that other enzymes can be used that can selectively hydrolyze the isolevuglandin and/or levuglandin phospholipid adducts to isolevuglandin and/or levuglandin phospholipid derivatives that can be detected by MS.

Advantageously, the iso-LG phospholipid adduct can be hydrolyzed in the presence of a chelating agent, such as ethylenediaminetetraacetic acid (EDTA), and/or an antioxidant, such as butylated hydroxytoluene (BHT), to inhibit oxidation of the -LG phospholipid adduct.

Following hydrolysis of the LG or iso-LG phospholipid adducts to form LG or iso-LG phospholipid derivatives, the LG or isoLG phospholipid derivatives can be extracted with a solvent, such as an organic solvent, to further isolate and/or separate the LG or isoLG phospholipid derivatives from the enzyme. In one aspect of the invention, the LG or isoLG phospholipid derivatives can be extracted with at least one organic solvent. The solvent can include, for example, methanol, chloroform, or a chloroform/methanol mixture (e.g., 1/2 v/v). It will be appreciated by one skilled in the art that the solvent is not strictly limited to this context, as the solvent may be used for the removal of LG or isoLG phospholipid derivatives from a liquid mixture, with which the liquid is immiscible in the solvent. Those skilled in the art will further understand and appreciate other appropriate solvents that can be employed to extract LG or isoLG phospholipid derivatives.

Following solvent extraction, the LG or isoLG phospholipid derivatives can be further purified by liquid chromatography (LC) prior to quantification using mass spectrometry. Liquid chromatography removes impurities and may be used to concentrate the LG or isoLG phospholipid derivatives for detection. Traditional LC relies on chemical interactions between sample components (e.g., LG or isoLG phospholipid derivatives) and a stationary phase such as a column packing. Laminar flow of the sample, mixed with a mobile phase, through the column is the basis for separation of the components of interest. The skilled artisan understands that separation in such columns is a partition process.

In various embodiments, one or more of the purification and/or analysis steps can be performed in an automated fashion. By careful selection of valves and connector plumbing, two or more chromatography columns can be connected as needed such that material is passed from one to the next without the need for any manual steps. In certain embodiments, the selection of valves and plumbing is controlled by a computer pre-programmed to perform the necessary steps. The chromatography system can also be connected in-line to the detector system, e.g., an MS system. Thus, an operator may place a tray of hydrolyzed and purified samples in an autosampler, and the remaining operations are performed under computer control, resulting in purification and analysis of all samples selected. In one embodiment, a diverter valve is placed in-line between the LC column and the interface with the MS. The diverter valve directs the LC effluent into a waste container until slightly prior to the time expected peak retention). This prevents the solvent front and other impurities from being passed into the MS device.

As used here, "in-line" refers to a configuration in which the LC and the ionization/injection device for the first MS quadropole are functionally connected in order that the LC effluent passes directly into the first MS device. "In-line" configurations may include a selector valve such that the effluent from two or more LC columns may be directed individually into the MS device and, optionally, to a waste container. Such a configuration is useful for a high throughput system and reduces the analysis time required for a large number of samples. High throughput systems may be designed in which an autosampler initiates LC purifications on the two or more LC columns at staggered intervals. In this way, the purified LG or isoLG phospholipid derivative peak is eluted from each LC column at a known interval. In certain embodiments, the purified LG or isoLG phospholipid derivatives peaks eluting from the two or more LC columns are directed into the MS device in rapid succession, but with sufficient temporal separation that individual measurements are not compromised. Such a high throughput system reduces the amount of "idle-time" for MS detection attributable to the LC procedure, which typically requires more time than the MS analysis.

By contrast, "off-line" refers to a configuration that requires manual intervention to transfer the LC effluent to the MS device. Typically, the LC effluent is captured by a fractionator and must be manually loaded into a MS device or into an autosampler for subsequent MS detection. Off-line configurations are useful, but less desirable because of the increased time required to process large numbers of samples.

LG or isoLG phospholipid derivatives purified by LC are conveniently detected and quantified by mass spectrometry (MS). The LG or isoLG phospholipid derivative-containing effluent from the LC is injected into an ionization chamber of the MS in which a first (parent) ion is produced. The parent ion may be detected directly in a first MS, or it may be isolated by the first MS, fragmented into characteristic daughter ions, and one or more of the daughter ions detected in a second MS (i.e., tandem MS).

The term "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z").

As used herein, the term "ionization" refers to the process of generating an analyte ion having a net electrical charge equal to one or more electron units. Negative ions are those having a net negative charge of one or more electron units, while positive ions are those having a net positive charge of one or more electron units.

The ions may be detected using several detection modes. For example, selected ions may be detected using a selective ion monitoring mode (SIM) which includes multiple reaction monitoring (MRM) or selected reaction monitoring (SRM). Alternatively, ions may be detected using a scanning mode.

In an aspect of the invention, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

"Tandem mass spectrometry," or "MS/MS" is employed to enhance the resolution of the MS technique. In tandem mass spectrometry, a parent ion generated from a molecule of interest may be filtered in an MS instrument, and the parent ion subsequently fragmented to yield one or more daughter ions that are then analyzed (detected and/or quantified) in a second MS procedure.

Collision-induced dissociation ("CID") is often used to generate the daughter ions for further detection. In CID, parent ions gain energy through collisions with an inert gas, such as argon, and subsequently fragmented by a process referred to as "unimolecular decomposition." Sufficient energy must be deposited in the parent ion so that certain bonds within the ion can be broken due to increased vibrational energy.

By careful selection of parent ions using the first MS procedure, only ions produced by certain analytes of interest are passed to the fragmentation chamber to generate the daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

The mass spectrometer typically provides the user with an ion scan; that is, the relative abundance of each m/z over a given range (e.g., 10 to 1200 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards (e.g., internal standards and external standards) can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of isolevuglandin and/or levuglandin phospholipid derivatives. Numerous other methods for relating the presence or amount of an ion to the presence or amount of the original molecule are well known to those of ordinary skill in the art.

The skilled artisan will understand that the choice of ionization method can be determined based on the analyte to be measured, type of sample, the type of detector, the choice of positive versus negative mode, etc. Ions can be produced using a variety of methods including, but not limited to, electron ionization, chemical ionization, fast atom bombardment, field desorption, and matrix-assisted laser desorption ionization (MALDI), surface enhanced laser desorption ionization (SELDI), photon ionization, electrospray ionization, and inductively coupled plasma. Electrospray ionization is a preferred ionization method. The term "electrospray ionization," or "ESI," as used herein refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated to prevent condensation and to evaporate solvent. As the droplets get smaller the electrical surface charge density increases until such time that, the natural repulsion between like charges causes ions as well as neutral molecules to be released.

Desirably, the effluent of the LC is injected directly and automatically (i.e., "in-line") into the electrospray device. In certain embodiments, the LG or isoLG phospholipid derivatives contained in the LC effluent is first ionized by electrospray into a parent ion of about 50 to about 900 m/z. The first quadrupole of the MS/MS is tuned to be a mass filter for the LG or isoLG phospholipid derivative parent ion (and/or the internal standard).

Parent ion(s) passing the first quadrupole are then ionized and/or fragmented prior to passing into the second quadrupole. In certain embodiments, the ions are collided with a inert gas molecule in a process of collision-induced dissociation (CID). Examples of inert gases include, for example, argon, helium, nitrogen, etc. Desirably, the LG or isoLG phospholipid derivative parent ion is fragmented into daughter ions having, for example, m/z=79, 153, 255, and 409. It is these daughter ions that are subsequently detected.

It is desirable to use one or more standards for calibration and quantification purposes. Internal and external standards are commonly used for these purposes. Internal standards are typically analogs of the compound(s) of interest that are expected to react similarly during all extraction and quantification steps. A known amount of an internal standard is typically added to each sample early in the processing in order to account for any loss of compound during any processing step. External standards typically consist of samples containing a known quantity of the compound of interest, or an analog, which are processed in parallel with the experimental samples. External standards are often used to control for the efficiency of the various processing steps. Finally, calibration standards are used to quantify the amount of the compound of interest in each experimental and external control sample. Typically, a series of calibration standards containing varying known amounts of the compound(s) of interest are injected directly into the detection device (i.e., the MS). Calibration standards are used to generate a standard curve, against which the experimental samples are quantified. These standards also may be used to determine limits of detection for any particular detection methodology.

Once the amount or level of the LG or isoLG phospholipid derivative is determined, the level of the at least LG or isoLG phospholipid derivative in the subject's bodily sample can be compared to a predetermined value or control value to provide information for determining the oxidative damage or oxidative injury in the subject or the tissue of the subject being measured. The predetermined value can be based upon the level or the LG or isoLG phospholipid derivative in comparable samples obtained from a healthy or normal subject or the general population or from a select population of healthy subjects. For example, the select population may be comprised of apparently healthy subjects. "Apparently healthy", as used herein, means have not demonstrated any signs or symptoms indicating the presence of oxidative injury or damage disease and would be characterized as healthy and free of symptoms of a disease associated with oxidative injury or disease.

The predetermined value can be related to the value used to characterize the level of the LG or isoLG phospholipid derivative in the bodily sample obtained from the test subject. Thus, if the level of the LG or isoLG phospholipid derivatives is an absolute value, such as the mass of the LG or isoLG phospholipid derivative of the bodily sample, the predetermined value can also be based upon the mass of the LG or isoLG phospholipid derivative in subjects in the general population or a select population of human subjects. Similarly, if the level of the LG or isoLG phospholipid derivatives is a representative value such as an arbitrary unit, the predetermined value can also be based on the representative value.

The predetermined value can take a variety of forms. The predetermined value can be a single cut-off value, such as a median or mean. The predetermined value can be established based upon comparative groups such as where the level of the LG or isoLG phospholipid derivative in one defined group is double the level of the LG or isoLG phospholipid derivatives in another defined group. The predetermined value can be a range, for example, where the general subject population is divided equally (or unequally) into groups, or into quadrants, the lowest quadrant being subjects with the lowest levels of the LG or isoLG phospholipid derivatives, the highest quadrant being individuals with the highest levels of the LG or isoLG phospholipid derivatives.

Predetermined values of the LG or isoLG phospholipid derivatives, such as for example, mean levels, median levels, or "cut-off" levels, are established by assaying a large sample of subjects in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each LG or isoLG phospholipid derivative that is assayed.

Alternatively, the level of the LG or isoLG phospholipid derivative can be compared to a predetermined value to provide a risk value, which characterizes the subject's risk of developing an oxidative injury.

The levels of the LG or isoLG phospholipid derivatives, in the subject's bodily sample may also be compared to a level of LG or isoLG phospholipid derivative obtained from a bodily of a sample previously obtained from the subject, such as prior to administration of therapeutic. Accordingly, the method of the present invention can be used measure the efficacy of therapeutic regimen in reducing oxidative damage in a subject by comparing the level of LG or isoLG phospholipid derivatives in bodily samples obtained before and after a therapeutic regimen. Additionally, the method of the present invention can be used to measure the progression of oxidative damage in a subject by comparing the level of LG or isoLG phospholipid derivatives in bodily samples obtained over a given time period, such as days, weeks, months, or years.

The present methods tests are useful in measuring oxidative damage, injury, or stress associated with for example, atherosclerosis, end stage kidney disease, myocardial infarction, glaucoma, hyperoxia, allergic inflammation, sepsis, macular degeneration, and liver injury. An increase oxidative can be used to determine the occurrence, progression, and/or risk of these and other pathologies in subjects. Accordingly, the method of the present invention can also be used to detect, measure the progression, and/or determine the risk of a subject developing or having a pathology associated with oxidative damage, such as atherosclerosis, end stage kidney disease, myocardial infarction, glaucoma, hyperoxia, allergic inflammation, sepsis, macular degeneration, and liver injury.

EXAMPLE 1

In this example, using a method based on reverse-phase high-performance liquid chromatography with online electrospray ionization tandem mass spectrometry, we confirmed that iso[4]$LGE_2$ covalently binds ethanolamine phospholipids in vitro to form covalent pyrrole adducts that are oxidized in air to deliver stable lactam and HL adducts (FIG. 1). These adducts could not be detected in biological samples. Because such adducts were expected to be present as a complex mixture in which the levels of individual species might not be sufficient for detection, we simplified the mixture by selective hydrolysis. In the event, phospholipase $A_2$ ($PLA_2$)-catalyzed hydrolysis of putative isoLG-diacyl-PE precursors in lipid extracts from human plasma and mouse liver allowed the detection of isoLGlysoPE-HL derivatives of isoLGs. To prevent in vitro oxidation, a transition metal ion chelator (EDTA) and the antioxidant butylated hydroxytoluene (BHT) were present at all stages of sample processing. This finding provides the key to a sensitive and rapid method for quantifying the level of LG/isoLG modification of ethanolamine phospholipids present in vivo. Notably, LC-MS/MS detection of isoLG-lysoPE-HLs is readily achieved with samples that are an order of magnitude smaller—e.g., 200-μl human plasma samples and 10-mg samples of mouse liver—and sample processing is much simpler and less time consuming than required for measuring protein-derived LG/isoLG-lysyl lactams. These features enhance the clinical utility of LG/isoLG-PE-HLs for assessing oxidative injury.

Materials and Methods

Materials

1-Palmitoyl-2-hydroxy-sn-glycero-3-phosphoethanolamine (lysoPE), 1,2-dipalmitoyl-D62-sn-glycero-3-phosphoethanolamine (D62-dP-PE), and 1-palmitoyl-2-arachidonoyl-sn-glycero-3-phosphocholine (PA-PC) were purchased from Avanti Polar Lipids (Alabaster, Ala., USA). $PLA_2$ (10,000 units/ml) from porcine pancreas (P0861) was obtained from Sigma-Aldrich (St. Louis, Mo., USA). Myeloperoxidase (MPO) was purchased from Calbiochem (La Jolla, Calif., USA). All other chemicals were purchased from Sigma-Aldrich. HPLC solvents were purchased from Aldrich (Milwaukee, Wis., USA) or Fisher Scientific (Pittsburgh, Pa., USA). Bicinchoninic acid protein assay reagent was purchased from Pierce (Rockford, Ill., USA). Female C57BL/6 mice (8-10 weeks of age) were purchased from The Jackson Laboratory (Bar Harbor, Me., USA). All reverse-phase HPLC columns were obtained from Phenomenex (Torrance, Calif., USA). Iso[4]LGE$_2$ was prepared by Dr. James Laird as described elsewhere.

Plasma from Age-Related Macular Degeneration and Control Patients

Clinically documented age-related macular degeneration and control blood donors were obtained from the Cole Eye Institute, Cleveland Clinic Foundation, with Institutional Review Board approval and according to Declaration of Helsinki principles. All patients received a comprehensive eye examination by a clinician in the Clinical Genomic and Proteomic AMD Study Group and provided written informed consent. Human identifiers were removed and the specimens encoded by the Clinical Study Group to protect donor confidentiality. Disease progression was categorized based on fundus examination, and advanced age-related macular degeneration patients with choroidal neovascularization (n=15) were included in the study. Control donors (n=15) lacked macular drusen and exhibited no clinical evidence of any retinal disorder. On average age related macular degeneration blood donors were 72.7 years of age (range 64-84) and control donors were 72.4 years of age (range 52-80); both cohorts included 7 female and 8 male donors. Plasma was prepared as described elsewhere in the presence of the antioxidant BHT (22 μg/ml plasma) and a protease inhibitor cocktail (Sigma Product P 8340; 10 μl/ml plasma), quench-frozen in liquid nitrogen, and stored at −80° C. under argon until analysis. All plasma samples were frozen and thawed only once.

General Methods

Proton magnetic resonance (1H NMR) spectra were recorded on a Varian Inova AS400 spectrometer operating at 400 MHz. Proton chemical shifts are reported in parts per million on the δ scale relative to deuterated chloroform (CDCl3; δ 7.24). Carbon magnetic resonance (13C NMR) spectra were recorded on a Varian Inova AS400 spectrometer at 100 MHz and chemical shifts are reported relative to CDCl3 (δ 77.0). All high-resolution mass spectra were recorded on a Kratos AEI MS25 RFA high-resolution mass spectrometer at 20 eV.

Chemical Synthesis of iso[4]LGE$_2$-lysoPE-hydroxylactam

Figure 12:
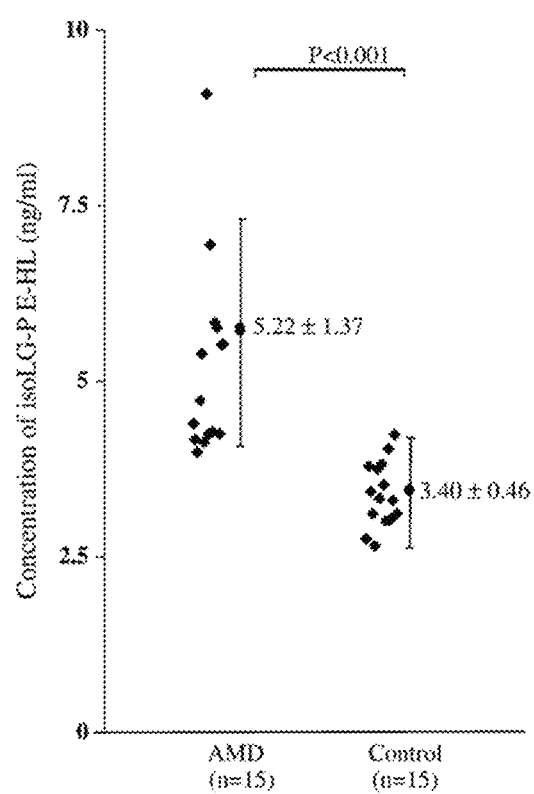
FIG. 12 illustrates levels of isoLG-lysoPE-hydroxylactam adducts in human plasma quantified by LC-MS/MS. Plasma samples were obtained from healthy normal donors (n=15) and from patients with advanced age-related macular degeneration (AMD; n=15). The mean level detected in age-related macular degeneration plasma (5.2±0.4 ng/ml, n=15 patients) was significantly elevated (P b 0.0001) compared with plasma from healthy volunteers (3.4±0.1 ng/ml, n=15).
Figure 13:
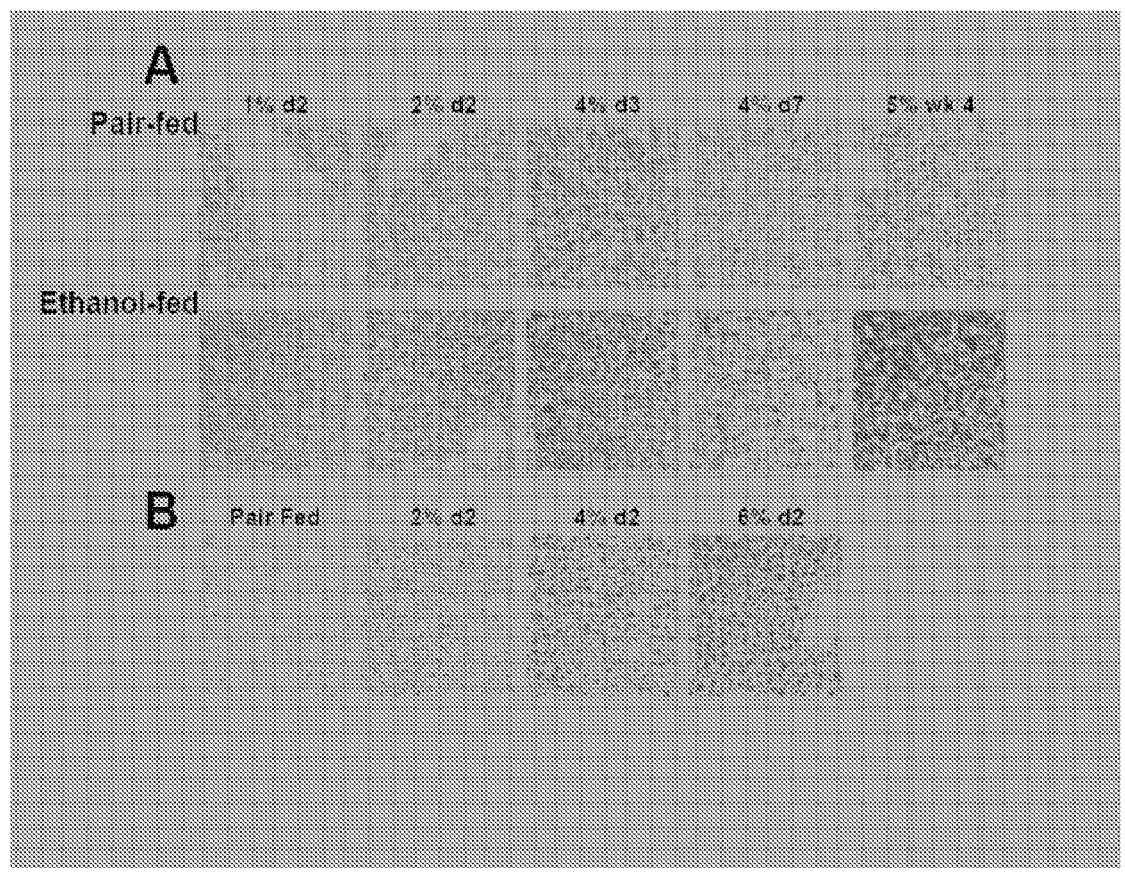
FIG. 13 illustrates the accumulation of neutral lipids in the liver of C57BL/6 mice after chronic or short-term ethanol feeding. Oil Red O staining was visualized in OCT embedded liver sections. A) Mice allowed free access to increasing concentrations of ethanol-containing diets or pair-fed control diets for 2 to 39 days. B) Mice were allowed free access to 1% ethanol-diet followed by increasing concentrations of ethanol-containing diets (2, 4 or 6%) for 2 days. Control animals received pair-fed diet which iso-calorically substituted with maltose-dextrins for ethanol. Images were acquired using 10× objective. Figures are representative of at least 3 mice in each experimental group.

A solution containing iso[4]LGE$_2$ (5 mM), 1-palmitoyl-2-hydroxysn-glycero-3-phosphatidylethanolamine (5 mM), and triethylamine (50 mM) in 1 ml of chloroform/methanol/water (60/35/5, v/v/v) was incubated with magnetic stirring under an oxygen atmosphere for 12 h at room temperature. The reaction was quenched by adding saturated aqueous ammonium chloride (500 μl). Then the mixture was extracted with methanol/chloroform (1/2, v/v, 3×1.5 ml), and the organic layer was concentrated to afford crude product. HPLC separation of the reaction products was performed using a 600 solvent delivery system (Waters, Wilmington, Del., USA) coupled to a 717 autosampler (Waters), a 2996 photodiode array detector (Waters), and a SEDEX 75 evaporative light scattering detector (Sedere, France) using a semipreparative Luna C18 (2) column (250×10 mm, 5 μm; Phenomenex). The mobile phase was created by mixing water/methanol (50/50, v/v) with 1 mM ammonium acetate (A) and water/methanol (5/95, v/v) (B) at a flow rate of 2 ml/min with the following gradients: 0-10 min A/B 100:0, 10-20 min a linear gradient from 100:0 to 50:50, 20-45 min 50:50, 45-46 min a linear gradient from 50:50 to 0:100, 47-77 min 0:100, 77-78 min a linear gradient from 0:100 to 100:0, 78-90 min 100:0. A fraction containing the hydroxylactam was collected from 59 to 61 min and characterized by hydrogen and carbon NMR (FIGS. 12 and 13). $^1$H NMR (400 MHz, CDCl$_3$), δ 7.12-6.94 (1H), 6.58-6.39 (1H), 5.72-5.55 (1H), 5.40-5.28 (1H), 4.43-3.88 (8H), 3.58-3.39 (1H), 3.39-3.20 (1H), 2.68-2.41 (6H), 2.12-1.94 (4H), 1.81-1.52 (7H), 1.05-1.39 (30H), 0.86 (t, 6H, J=6.8 Hz). $^{13}$C NMR (100 MHz, CDCl$_3$), δ 176.20 (CO), 172.10 (CO), 171.95 (CO), 170.82 (CO), 155.91 (C), 155.82 (C), 137.97 (CH), 135.42 (CH), 135.20 (CH), 126.23 (CH), 126.20 (CH), 124.38 (CH), 124.34 (CH), 120.12 (CH), 119.88 (CH), 87.50 (C), 87.39 (C), 72.14 (CH), 72.02 (CH), 66.03 (CH$_2$), 65.52 (CH$_2$), 64.41 (CH$_2$), 63.43 (CH$_2$), 47.12 (CH$_2$), 39.21 (CH$_2$), 35.98 (CH$_2$), 32.22 (CH$_2$), 32.07 (CH$_2$), 29.43 (CH$_2$), 28.95 (CH$_2$), 28.50 (CH$_2$), 24.55 (CH$_2$), 24.21 (CH$_2$), 22.67 (CH$_2$), 22.02 (CH$_2$), 14.07 (CH$_2$).

Mass spectrometric characterization of the iso[4]LGE$_2$-lysoPE-HL is presented under Results together with that of the corresponding pyrrole and lactam adducts present in the reaction product mixture. To determine the yields of these iso[4]LGE$_2$ adducts, a calibration curve for the HL was generated from mixtures containing a fixed amount (2 ng) of internal standard (iso[4]LGE$_2$-D31-lysoPEHL) and various amounts of the iso[4]LGE$_2$-lysoPE-HL and by plotting peak area ratio vs analyte concentration (y=0.1100x+0.0062, $R^2$=0.9995). The yield of hydroxylactam adduct was 36%. Yields of lactam (26%) and pyrrole (2%) adducts were approximated using the hydroxylactam calibration curve.

Chemical Synthesis of iso[4]LGE$_2$-D3'-lysoPE-HL Internal Standard

Figure 14:
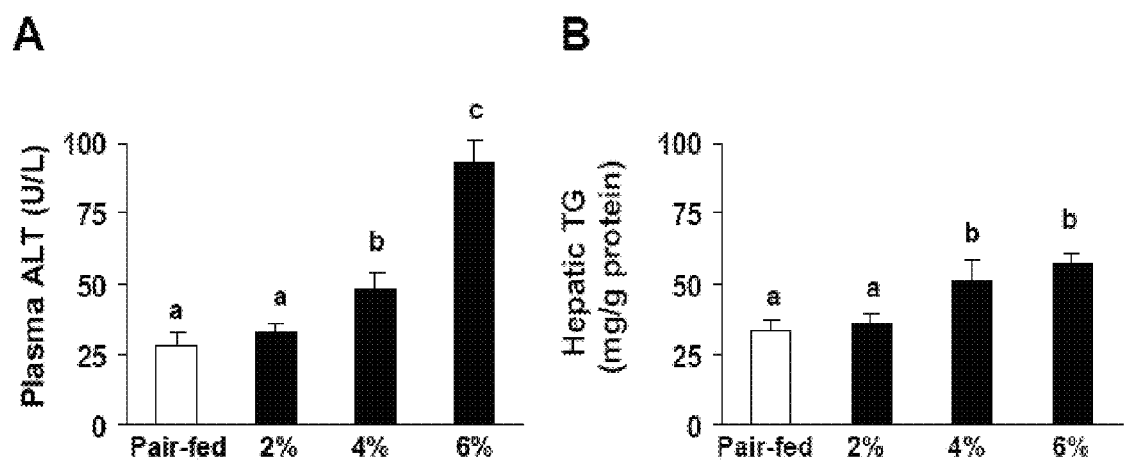
FIG. 14 illustrates plasma ALT activity and hepatic triglyceride content measurement in response to short-term ethanol feeding. Mice were allowed free access to 1% ethanol-diet followed by increasing concentrations of ethanol-containing diets (2, 4 or 6%) for 2 days. Control animals received pair-fed diet which iso-calorically substituted with maltose-dextrins for ethanol. A) Plasma ALT activity and B) hepatic triglyceride contents were measured. Values represent means±SEM, n=4. Groups with different alphabetical superscripts differ significantly (p<0.05).
Figure 15:
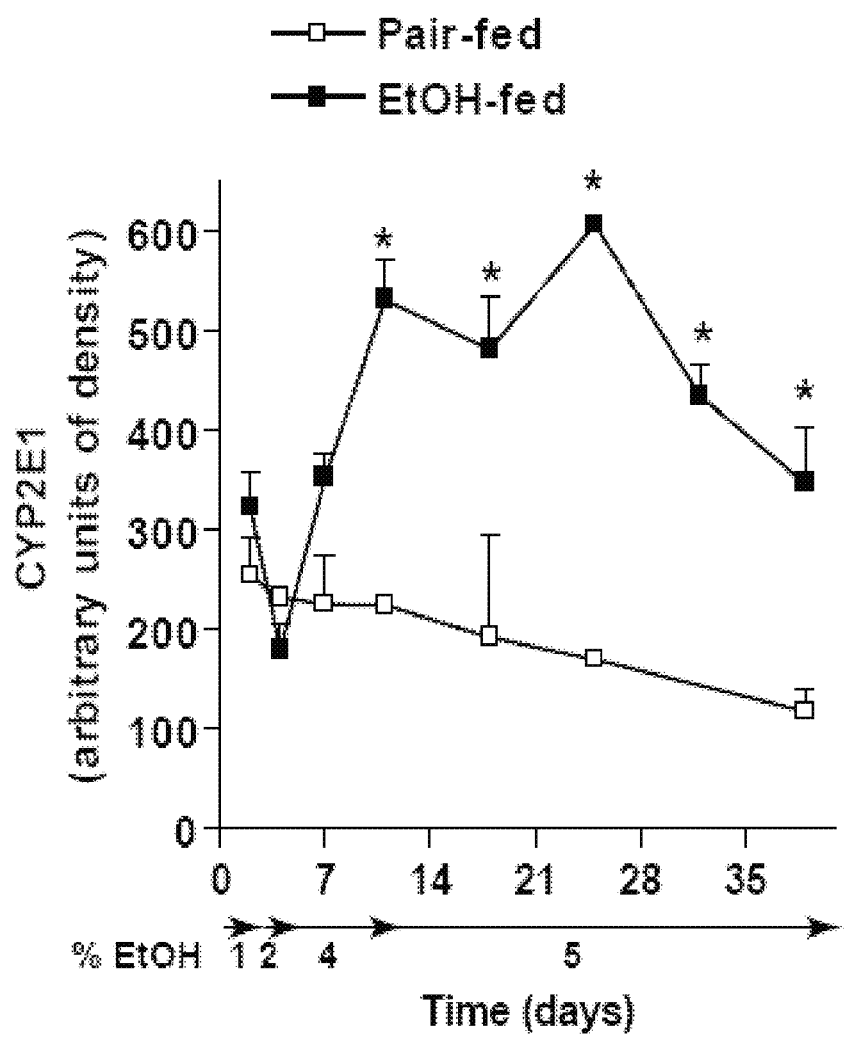
FIG. 15 illustrates CYP2E1 expression was elevated in mouse livers after chronic ethanol feeding. Homogenates were prepared from livers of ethanol- and pair-fed mice allowed free access to increasing doses of ethanol feeding and the expression of CYP2E1 assessed by Western blot analysis. Values represent means±SEM, n=4, *p<0.05 was considered as significant.

Iso[4]LGE$_2$-D62-dP-PE-HL was prepared analogously to the synthesis of iso[4]LGE$_2$-lysoPE-HL using D62-dP-PE in place of 1-palmitoyl-2-hydroxy-sn-glycero-3-phosphoethanolamine. Iso[4]LGE$_2$-D31-lysoPE-HL was then obtained by selective lipolysis catalyzed by PLA2. A solution in methanol of crude iso[4]LGE$_2$-D62-dP-PEHL (100 μl containing 50 mg/ml) was added to phosphate-buffered saline (PBS; 1 ml, 10 mM, pH 7.4) containing CaCl$_2$ (5 mM). The resulting mixture was sonicated for 10 min followed by the addition of PLA2 (100 μl). The resulting mixture was incubated at 37° C. for 10 h under argon. Then the product mixture was extracted three times with (3×1.5 ml) methanol/chloroform (1/2, v/v). Solvents were evaporated from the organic layer under a stream of dry argon. The residue was dissolved in methanol/water (1/1, v/v) and subjected to the same protocol of HPLC separation as described above for purification of iso[4]LG-lysoPE-HL. Pure iso[4]LGE$_2$-D31-lysoPE-HL was isolated in 23% overall yield and characterized by proton NMR (FIG. 14) and mass spectrometry (FIG. 15). $^1$H NMR (400 MHz, CDCl$_3$), δ 7.14-6.95 (1H), 6.59-6.35 (1H), 5.66-5.54 (1H), 5.39-5.31 (1H), 4.30-3.82 (8H), 3.59-3.14 (2H), 2.38-2.23 (6H), 2.09-1.93 (2H), 1.92-1.39 (5H), 1.31-1.10 (6H), 0.87 (t, 3H, J=6.8 Hz).

Time Course of the Reaction Between iso[4]LGE2 and lysoPE

The time course of the reaction between iso[4]LGE$_2$ and lysoPE was determined. Synthetic iso[4]LGE$_2$ (5 mM) was incubated with 1-palmitoyl-2-hydroxy-sn-glycero-3-phosphatidylethanolamine (5 mM) in chloroform/methanol/water (2 ml of 60/35/5, v/v/v) containing triethylamine (50 mM). The mixture was stirred under an oxygen atmosphere at room temperature. Aliquots (200 μl) were withdrawn at various times, and the reaction was quenched by adding 100 μl of saturated aqueous ammonium chloride. Then the resulting mixture was extracted with methanol/chloroform (1/2, v/v, 3×1.5 ml) and the organic layer was concentrated to afford crude product, which was analyzed by LC-MS/MS.

Free Radical-Induced Oxidation of PA-PC with lysoPE

Small unilamellar vesicles comprising PA-PC (0.2 mg/ml) and lysoPE (0.8 mg/ml) were prepared by extrusion (10 times) through a 0.1-μm polycarbonate filter using an Avanti miniextruder (Avanti Polar Lipids) in argon-sparged PBS (50 mM, pH 7.0, supplemented with 200 μM diethylenetriamine pentaacetic acid). The vesicles were oxidized by exposure to glucose oxidase (100 ng/ml), glucose (100 μg/ml), sodium nitrite (500 μM), and MPO (30 nM) as described previously. The small unilamellar vesicle solution (2.5 ml) was incubated at 37° C. for 24 h. The oxidation reaction was terminated by the addition of BHT in ethanol (50 μl of 2 mMin ethanol to give 40 μM final concentration) and catalase (125 μl of 1.5 mg/ml in water to give 300 nM final concentration) to the reaction mixture and then extracted immediately by the Bligh and Dyer method. After evaporation of the solvent under a stream of dry argon, the residue was subjected to PLA2-catalyzed hydrolysis. Thus, the extract was dissolved in methanol (50 μl). Then 450 μl of PBS solution (10 mM, pH 7.4) and 50 μl of $CaCl_2$ (50 mM) were added. The resulting mixture was sonicated for 10 min followed by the addition of 50 μl of PLA2 (10,000 unit/ml). After incubation at 37° C. for 10 h under argon, the resulting mixture was extracted three times with 750 μl of methanol/chloroform (1/2, v/v). Solvents were evaporated under a stream of argon and stored in vials sealed under argon at −80° C. before being analyzed using LC-MS/MS.

Extraction of Plasma Lipids

Plasma samples were extracted by a modified Bligh and Dyer method adapted for small scale with precautions (addition of BHT and EDTA) to prevent in vitro oxidation. In brief, plasma (200 μl) was mixed with 750 μl of chloroform/methanol (1/2, v/v) containing 1 mM BHT. For LC/MS analysis, 2 or 2.6 ng of internal standard (iso[4]$LGE_2$-D31-lysoPE-HL) was included in this solution. The resulting mixture was vortexed for 15 min to maximize the extraction efficiency. Chloroform (250 μl) was added and the mixture was vortexed for 1 min. Then aqueous sodium chloride (250 μl of 1.5%) was added and the mixture was vortexed for 1 min. The resulting mixture was centrifuged (3000 rpm) for 10 min to give a three-phase system (aqueous top, protein disk, organic bottom). The bottom layer was carefully withdrawn with a polyethylene transfer pipette (Fisher Cat. No. 13-711-31), making sure to avoid the interface or upper layer. The solvents were then evaporated under a stream of argon at room temperature, and the sample was stored under argon at −80° C. before being analyzed using LC-MS/MS.

Extraction of Tissue Lipids

Liver samples from chronic ethanol-fed mice (C57BL/6 female) and control mice pair-fed diets that isocalorically substituted maltose dextrins for ethanol were prepared as described in a companion paper. The liver tissue was extracted by the method of Folch et al. Tissue was placed in a tube with chloroform/methanol (2/1, v/v) containing 1 mM BHT and 10 ng/ml internal standard iso[4]$LGE_2$-D31-lysoPE-HL (2 ml of Folch solution per 100 mg of tissue). The tissue was homogenized manually using a Teflon-coated stainless steel pestle. After homogenization, the resulting mixture was placed in a 4° C. freezer for 30 min to maximize the lipid extraction efficiency. An aqueous solution of sodium chloride (1.5%, w/w, 1/4 the volume of the organic extract) was added. The resulting mixture was centrifuged at 3000 rpm for 15 min. The lower layer containing the lipids was carefully withdrawn with a polyethylene transfer pipette, making sure to avoid the interface or upper layer. The solvents were then evaporated under a stream of dry argon at room temperature, and the sample was stored under argon at −80° C. before being analyzed using LC-MS/MS.

$PLA_2$-Catalyzed Hydrolysis of Esterified isoLG-lysoPE Adducts from Biological Samples Time Course of the $PLA_2$-Catalyzed Hydrolysis of the Lipid Extract from a Plasma Sample The total lipid extract from 2 ml of plasma was dissolved in methanol (500 μl) followed by the addition of PBS solution (5 ml of 10 mM, pH 7.4) containing CaCl2 (5 mM). The resulting mixture was sonicated for 5 min followed by the addition of PLA2 (500 μl of 10,000 units/ml). The resulting mixture was incubated under argon at 37° C. Aliquots (600 μl) were withdrawn at various times and extracted immediately by the method of Bligh and Dyer (see Extraction of plasma lipids, above), the solvent was evaporated under a stream of dry argon, and the lipids were stored in vials under argon at −80° C. until LC-MS/MS analysis.

Processing of Biological Phospholipid Extracts

The total lipid extract from biological samples (200 μl of plasma or 100 mg of tissue) was dissolved in methanol (50 μl) followed by the addition of a PBS solution (10 mM, pH 7.4, 450 μl) containing CaCl2 (5 mM). The resulting mixture was sonicated for 5 min followed by the addition of PLA2 enzyme (50 μl of 10,000 units/ml). The resulting mixture was incubated under argon at 37° C. Aliquots (200 μl) were withdrawn at various times and extracted immediately by the Bligh and Dyer method (see Extraction of plasma lipids, above) and stored in vials under argon at −80° C. before LC-MS/MS analysis.

Overall Recovery after the Sample Pretreatment Steps

To assess the recovery of iso[4]$LGE_2$-lysoPE-HL from plasma, pure synthetic iso[4]$LGE_2$-lysoPE-HL (10 μl of 0.2 μg/ml in methanol) was added to plasma (200 μl). Then the mixture was extracted by the Bligh and Dyer method as described for extraction of plasma total lipids. The extract was dissolved in 50 μl of methanol followed by the addition of 450 μl of PBS solution (10 mM, pH 7.4). The resulting mixture was sonicated for 5 min. Note that the addition of PLA2 and $CaCl_2$ was omitted to avoid generation of additional iso[4]$LGE_2$-lysoPE-HL from endogenous phospholipids in the plasma. The resulting mixture was then extracted again by the Bligh and Dyer method. After evaporation of the solvents under a stream of dry argon, the final extract was dissolved in methanol (200 μl) containing iso[4]$LGE_2$-D31-lysoPEHL (2 ng as internal standard). The resulting mixture (20 μl) was quantitated by LC-MS/MS. Pure synthetic iso[4]$LGE_2$-lysoPE-HL 1542 W. Li et al./Free Radical Biology & Medicine 47 (2009) 1539-1552 10 μl of 0.2 μg/ml in methanol) was added to 200 μl of methanol containing iso[4]$LGE_2$-D31-lysoPE-HL (2 ng as internal standard). The resulting mixture (20 μl) was quantitated by LC-MS/MS. Recovery was determined by the ratio of iso[4]$LGE_2$-lysoPE-HL concentration after sample pretreatment to that without extraction.

Derivatization of Synthetic or Endogenous isoLG-lysoPE-HL

Pentafluorobenzyl ester derivatives of lipids were prepared by suspending the synthetic isoLG-lysoPE-HL (40 μg) or lipid extract from human plasma (200 μl) in anhydrous acetonitrile containing 10% pentafluorobenzyl bromide (PFB-Br) and 20% N,N-diisopropylethylamine (500 μl) at room temperature for 1 h. Solvent and volatile reagents were then evaporated under a stream of argon. Nonlipid components were removed by solid-phase extraction: the product mixture was transferred with 50% methanol in water (2×1 ml) and loaded on a C18 minicolumn (Strata C18-T solid-phase extraction tubes, 6 ml; Phenomenex). Nonlipid components were then removed by eluting with 75% methanol in water (6 ml). The lipid derivatives were then eluted with methanol (2 ml), and the solvents were evaporated under a stream of dry argon.

Mass Spectrometry

Direct infusion MS and LC-MS/MS were performed on a Quattro Ultima triple-quadrupole mass spectrometer (Micromass, Wythenshawe, UK). The tuning parameters of the mass spectrometer were optimized for each MS/MS transition by utilization of synthetic standards. The total ion current was measured in the mass-to-charge ratio (m/z) range of 50-900 at 30 V of cone energy in the negative ion mode with a 3.5-kV electrospray capillary voltage, 60-V cone voltage, 120° C. source temperature, 250° C. desolvation temperature, 65 L/h cone gas flow, and 658 L/h desolvation gas flow. A parent-to-daughter ion transition of m/z 800.2→153 was monitored for iso[4]LG-lysoPEHLs (collision energy 45 eV), 784.2→153 for iso[4]LG-lysoPE-lactam (collision energy 55 eV), 768.2→153 for iso[4]LG-lysoPE-pyrrole (collision energy 50 eV), and 831.2→153 for iso[4]LGE$_2$-D31-lysoPEHL internal standard (collision energy 40 eV) as quantifier for the multiple reaction monitoring (MRM) with a dwell time of 200 ms. Chromatographic separation was achieved using a Luna C18 column (150×2.0-mm i.d., 5-μm particle size; Phenomenex) connected to a Waters Alliance 2690 (Waters) HPLC system (pump and autosampler) for injection of the samples. Samples were eluted with a binary solvent gradient (methanol as solvent A and water as solvent B, with both mobile phases supplemented with 2 mM ammonium acetate to enhance the MS signal). A linear gradient was run from 75 to 100% solvent A over 10 min. After this solvent composition was held for 7 min, the mobile phase was linearly changed back to the initial mobile phase composition (75% methanol in water) over 0.5 min, and the column was equilibrated under this condition for 7.5 min before the next injection. A flow rate of 0.2 ml/min and a run time of 25 min were used for all analyses. All retention times of analytes shown in MRM spectra were recorded relative to the internal standard (iso[4]LGE2-D31-lysoPE-HL, 11.83 min). Lipid extracts from biological matrices were reconstituted with methanol (200 μl). An aliquot (20 μl) of the solution was employed for each LC-MS/MS analysis. We chose 800.2→153.0, the transition with the strongest intensity, for quantitation of isoLG-PE-HLs in biological matrices. The concentration of the isoLG-lysoPE-HLs in samples was determined by interpolation from the peak area ratio of iso[4]LGE$_2$-D31-lysoPE-HL versus isoLGlysoPE-HLs using a standard curve for iso[4]LGE$_2$-lysoPE-HL as described above. MS/MS data analyses were performed with Masslynx software (version 3.5; Waters Micromass).

Statistics

The data represent the means±SD of the indicated numbers of samples. The statistical analyses were made using a Student t test (two-sample assuming equal variances). For all of these hypotheses, the significance level was 0.05.

Results and Discussion

Figure 2A:
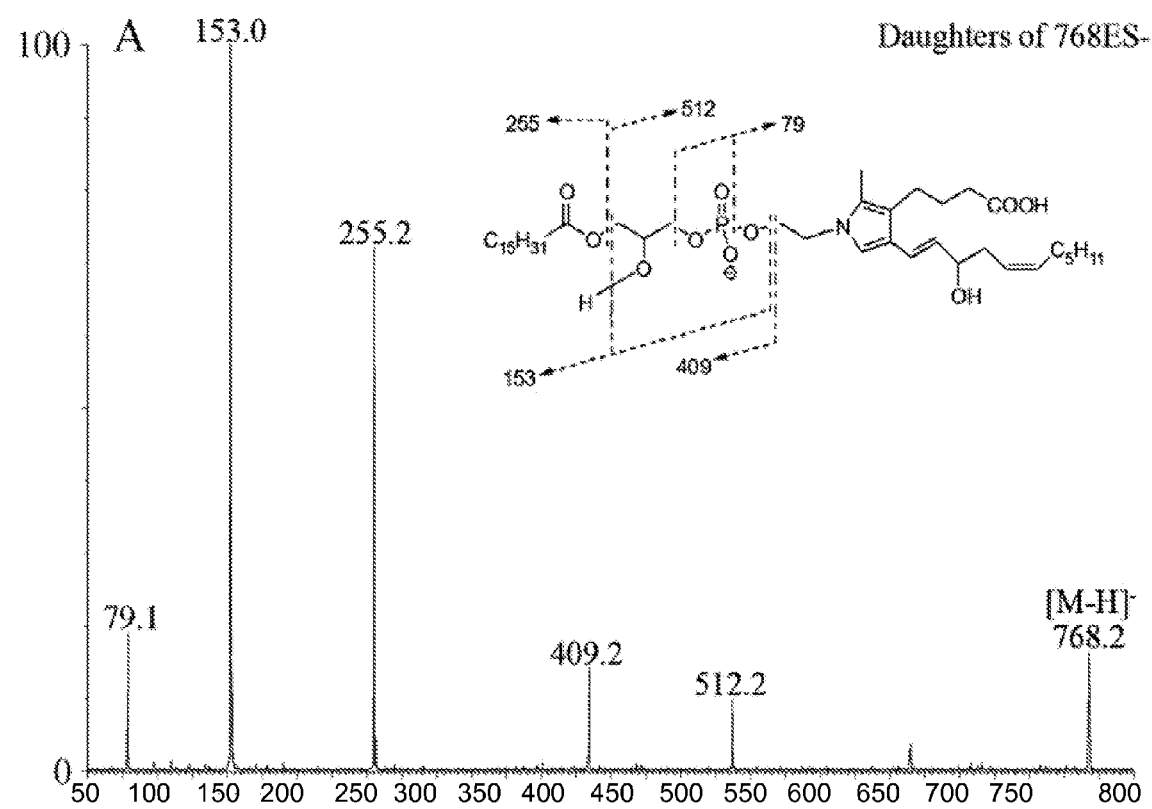
FIG. 2 are mass spectra illustrating collision-induced decomposition of electrospray-generated [M-H]$^-$ ions from iso[4]LGE$_2$-lyso-PE adducts: (A) Pyrrole adduct; (B) lactam adducts; (C) hydroxylactam adducts.
Figure 2B:
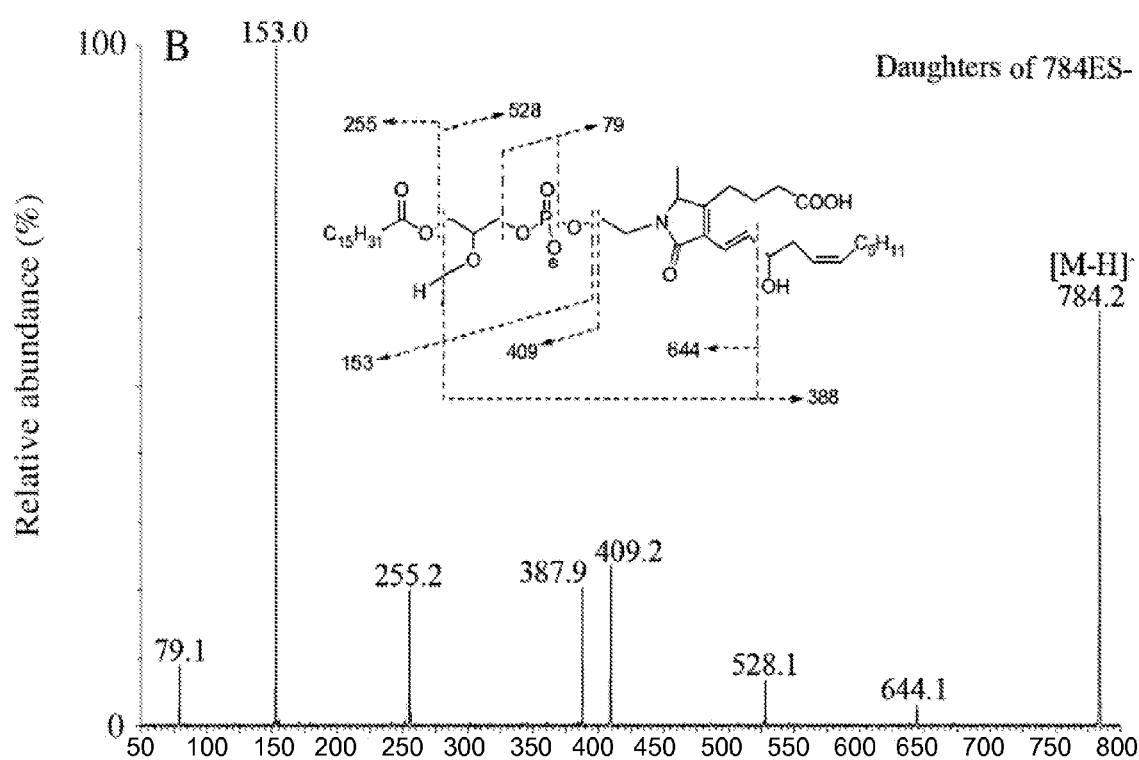
Figure 2C:
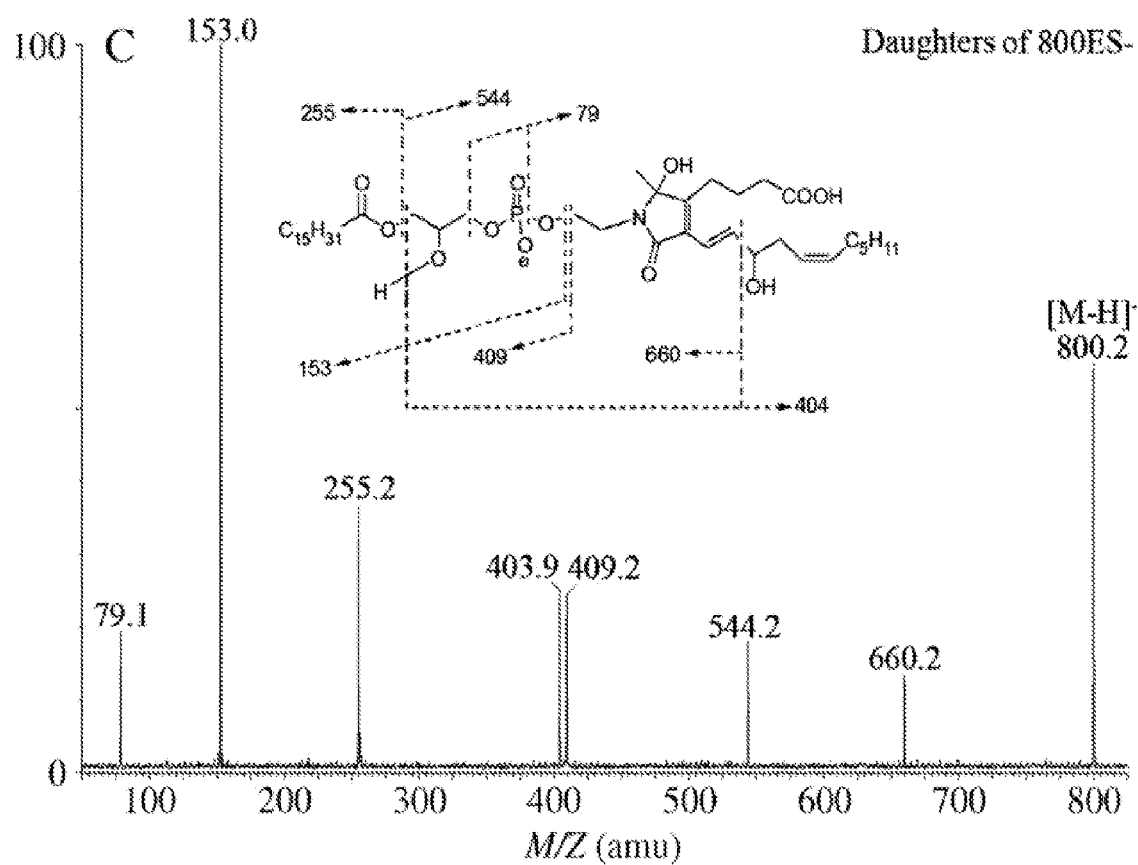

Mass Spectrometric Characterization of Covalent Adducts of Iso[4]LGE$_2$ with 2-lysoPE Pyrrole (MW 769), lactam (MW 785), and hydroxylactam adducts (MW 801) generated in the reaction of iso[4]LGE$_2$ with 2-lysoPE were analyzed by direct infusion MS in the negative ion mode. Representative collision-induced dissociation (CID) spectra of the three adducts are shown in FIG. 2. The CID fragments with m/z 79, 153, 255, and 512 (FIG. 2A) are precedented. The structure of the fragment ion with m/z 409 is deduced by analogy with a fragmentation mechanism suggested previously. The structures of daughter ions at m/z 528 (FIG. 2B) and 544 (FIG. 2C) are deduced by analogy to the daughter ion at m/z 512. The daughter ions at m/z 388, 644 (FIG. 2B) and 404, 660 (FIG. 2C) are deduced by analogy with a fragmentation mechanism suggested previously.

The fragments with m/z 79, 153, 255, and 409 in the pyrrole (FIG. 2A), lactam (FIG. 2B), and hydroxylactam (FIG. 2C) all correspond to isoLG-lysoPE adducts but do not distinguish isoLG structural isomers. The ion at m/z 79 indicates the formation of the phosphate-derived ion. The daughter ion at m/z 153 represents the combined losses of the palmitic acid and the isoLG-ethanolamine moiety. An ion at m/z 255 represents a palmitate anion from the sn-1 position. A fragment ion at m/z 409 corresponds to neutral loss of the isoLG-ethanolamine moiety. Daughter ions at m/z 512, 528, and 544 correspond to the loss of the sn-1 palmitoyl moiety from pyrrole, lactam, and hydroxylactam adducts, respectively (FIG. 2). The daughter ions at m/z 388 and 644 are unique for lysoPE-lactam adducts of iso[4]LGE$_2$ (FIG. 2B), whereas the daughter ions at m/z 404 and 660 are unique for the lysoPE-HL adduct of iso[4]LGE$_2$ (FIG. 2C). Diagnostic daughter ions with side-chain isomer-specific structural information, e.g., at m/z 372 and 628, which represent the sidechain fragment from iso[4]LGE$_2$-lysoPE-pyrrole, were not observed in the CID MS of the pyrrole adduct.

The pure hydroxylactam, isoLG-lysoPE-HL, was isolated by preparative HPLC from the mixture of adducts generated in the reaction of iso[4]LGE2 with lysoPE. The hydroxylactam was further characterized by NMR (FIG. 1). For the quantification of the level of isoLG adducts of lysoPE generated in vitro or in vivo, we synthesized an isotope-labeled hydroxylactam adduct, iso[4]LGE$_2$-D31-lysoPE-HL, which was also characterized by NMR and LC-MS/MS.

Figure 3:
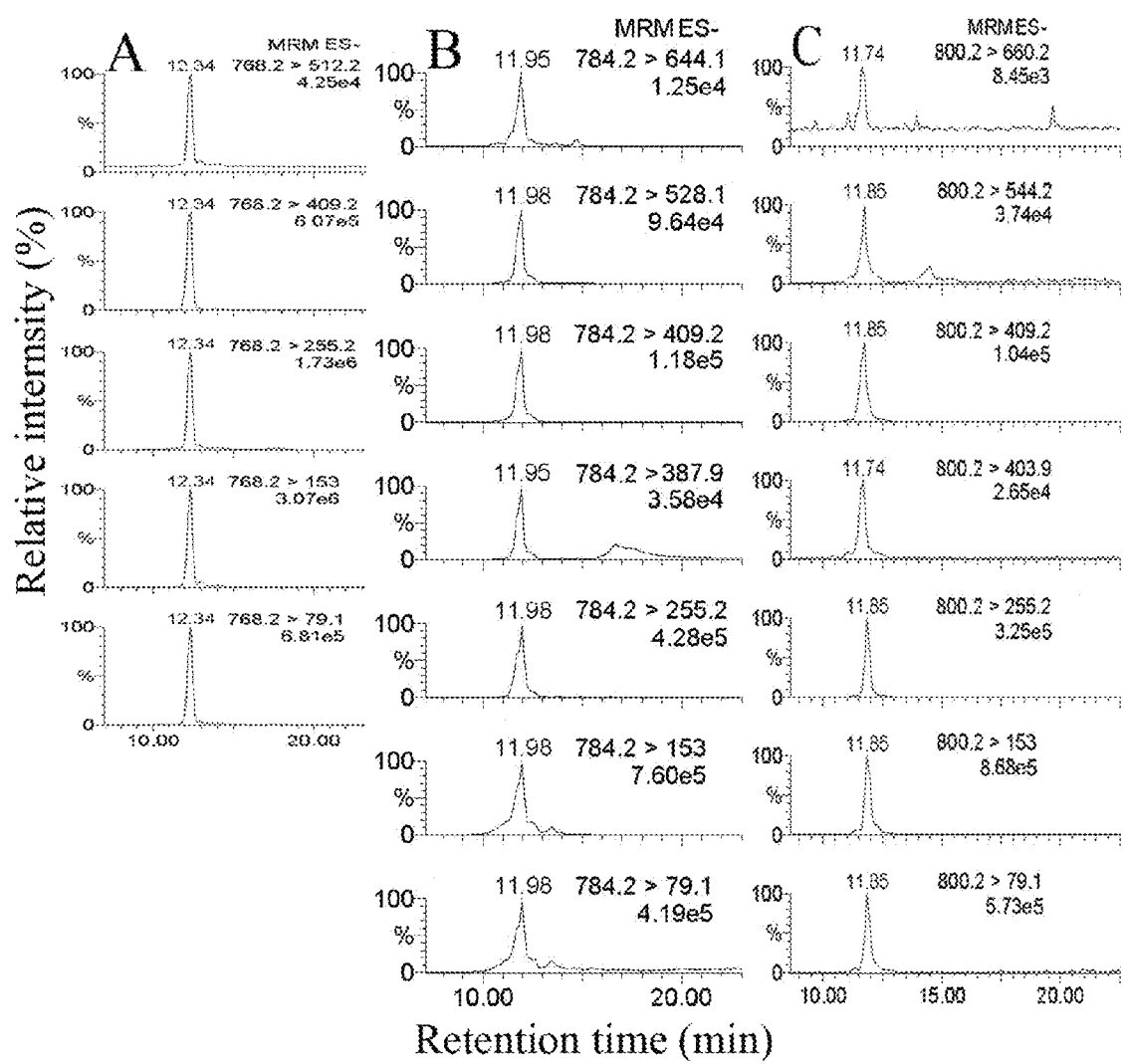
FIG. 3 are histograms illustrating LC/ESI/MS/MS analysis of iso[4]LGE$_2$-lyso-PE adducts: (A) pyrrole adducts; (B) lactam adducts; (C) hydroxylactam adducts.

The above results provided an LC-MS/MS method to simultaneously identify and quantify individual iso[4]LGE$_2$-lysoPE adducts. Pyrrole adducts were detected by MRM of the transitions between five daughter ions common to all isoLG structural isomers and the parent ions at m/z 768. Lactam and hydroxylactam adducts of iso[4]LGE$_2$ and lysoPE were detected by MRM of the transitions between the parent ions from lactam and hydroxylactam adducts, respectively, and five daughter ions common to all isoLG structural isomers as well as two daughter ions diagnostic of the unique side chains of iso[4]LG structural isomers (FIG. 3).

Figure 4:
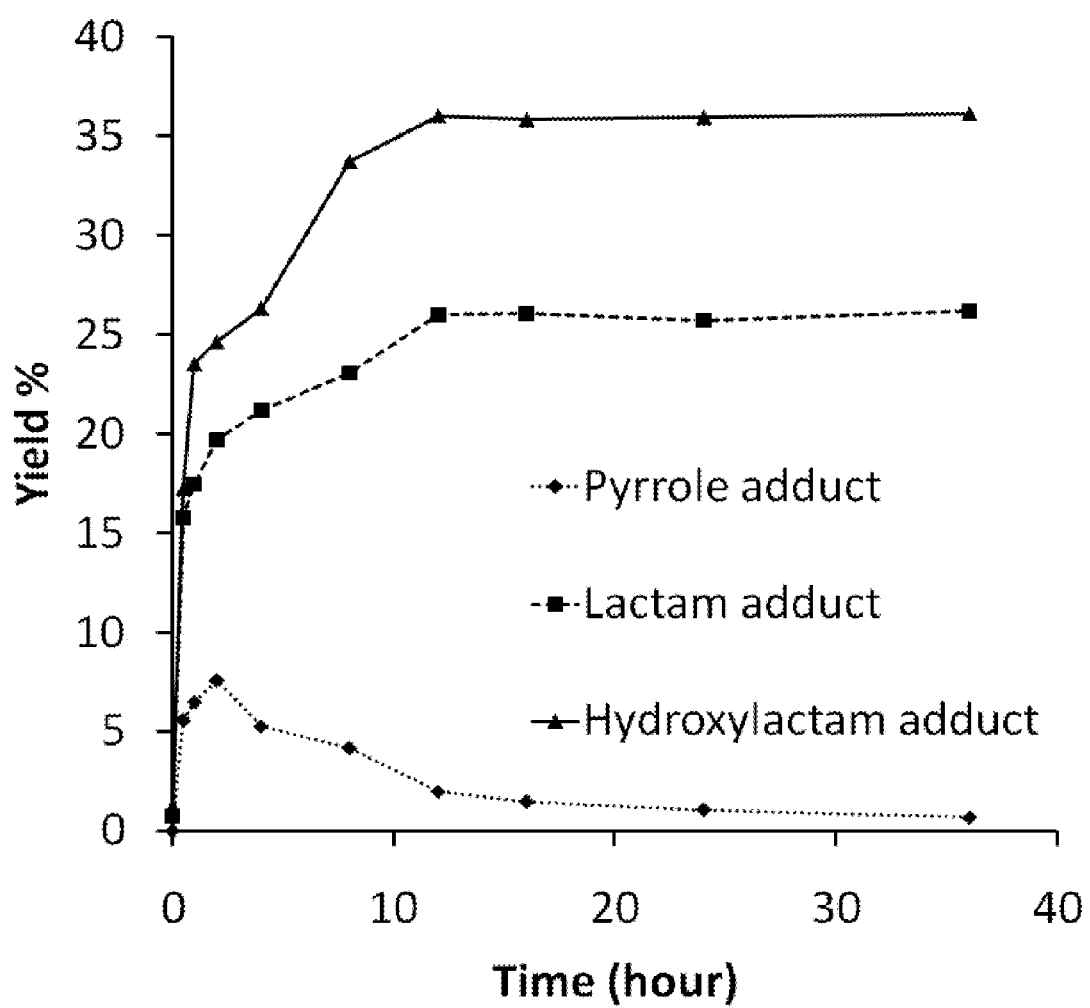
FIG. 4 is a plot illustrating time course of formation of iso[4]LGE$_2$-lyso-PE adducts using LC/MS quantitation methods. Data are expressed as means of experiments (n=3).

Time Course for the Formation of Covalent Adducts of iso[4]LGE$_2$ with 2-lysoPE The results of a study of the time course of the reaction between iso[4]LGE$_2$ and lysoPE are shown in FIG. 4. Initially the yield of the pyrrole climbs, but then it drops after 2 h, as expected for an intermediate in the production of the lactam and hydroxylactam adducts. After incubation for 36 h, the hydroxylactam (iso[4]LGE$_2$-lysoPE, 36%) and lactam (26%) are the major covalent adducts of iso[4]LGE$_2$ with lysoPE. The final yield of pyrrole adduct is very low because of its proclivity to autoxidation to give lactams and hydroxylactams.

Figure 5:
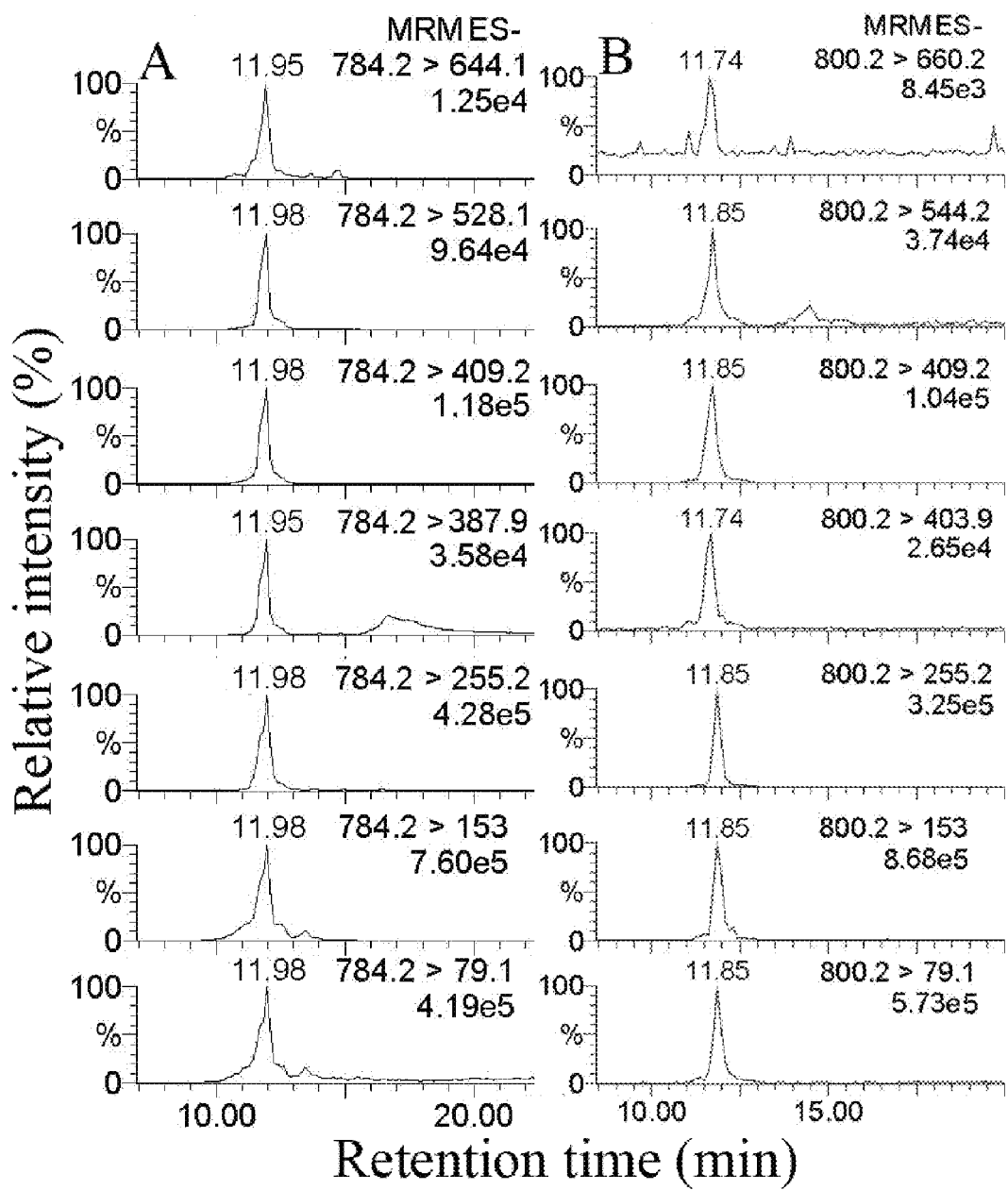
FIG. 5 are histograms illustrating LC/ESI/MS/MS analysis of putative iso[4]LGE$_2$-lyso-PE adducts generated during oxidation of AA-PC in vitro by incubation with MPO/G-GOX/NO$_2^-$ system and lysoPE.

Formation of isoLG-lysoPE-lactams and isoLG-lysoPE-hydroxylactams During MPO-Catalyzed Oxidation of PA-PC in the Presence of lysoPE The LC-MS/MS method described above was used to show that isoLG-lysoPE adducts can be generated in vitro using a well-defined and biologically relevant model system for lipid oxidation. We exposed PA-PC to the MPO/glucose(G)-glucose oxidase/NO$_2$-oxidation system in the presence of lysoPE and examined the reaction mixture for the presence of isoLG-lysoPE adduct. As shown in FIG. 5, the MPO-catalyzed oxidation of PA-PC in the presence of lysoPE, followed by PLA$_2$-catalyzed hydrolysis, generated both isoLG-lysoPE-lactam and isoLG-lysoPE-HL adducts that demonstrated the same retention times for the selected transitions between parent and daughter ions as the authentic standard iso[4]LG-lysoPElactam and iso[4]LG-lysoPE-HL adducts shown in FIG. 3. A careful inspection of the data in FIGS. 3 and 5 reveals considerable variations in the ratios of major chromatographic peaks. For example, for the isoLG-lysoPE-HL, relative to the 800→153 transition, the 800→79 transition is 15% in FIG. 3C and 66% in FIG. 5B and the 800→255 transition is 50% in FIG. 3C and 37% in FIG. 5B. By implementing the isotope dilution technique, a major improvement in precision was achieved. For example, for the isoLGlysoPE-HL after internal standard correction, relative to the 800→153 transition, the 800→79 transition is 15% in FIG. 3C and 14% in FIG. 5B and the 800→255 transition is 50% in FIG. 3C and 48% in FIG. 5B. This supports the conclusion that the imprecision of the uncorrected peak ratios is caused by variations from one LC-MS/MS run to another in collision energy, cone voltage, or other factors that change ionization efficiency (parent ions) or fragmentation efficiency (daughter ions) rather than, e.g., a consequence of an interfering compound present in the MPO-derived sample. The isotope dilution technique contributes significantly to the precision of the quantitative analysis of isoLG-lysoPE-HLs by LC-MS/MS.

Collectively, these results indicated that isoLGs generated from free radical-induced oxidation of arachidonate-containing phospholipids covalently bind phosphatidylethanolamine species in vitro and led to the expectation that these adducts are formed in vivo.

Initially No isoLG-lysoPE Adducts were Detected in Lipid Extracts from Human Plasma For detecting their presence in vivo, we initially examined whether isoLG-lysoPE-lactam and isoLG-lysoPE-HL adducts could be detected in the total lipid extract from human plasma samples from healthy individuals. We could not find the peaks in the MRM transitions representing lactam and hydroxylactam adducts. Furthermore, none of the MRM channels anticipated for isoLG-modified dP-PE, PO-PE, PL-PE, PA-PE, or PD-PE species provided any detectable signal (data not shown). We reasoned that the lack of detection of isoLG-phospholipid adducts under the initial conditions might be a consequence of their presence as a complex mixture of homologs containing a large variety of acyl groups esterified to the sn-2 hydroxyl group, none of which is present in adequate concentrations to provide a detectable signal.

Detection of isoLG-lysoPE-HLs in Lipid Extracts from Human Plasma after $PLA_2$ Treatment Although the isoLG moieties of the expected adducts are anticipated to comprise eight structural isomers, this isomerism will not interfere with the MS analysis because all of these isomers have the same molecular weight and are expected to have similar HPLC elution times. Furthermore, in the glycerophosphoethanolamine moiety, the sn-1 position is usually bound with saturated acyl groups, predominately palmitic acid (16:0) with lesser amounts of stearic acid (18:0). However, the sn-2 position may be esterified with a variety of saturated or unsaturated fatty acyls. This variance in sn-2 acyl groups of glycerophospholipid moieties affords a complex mixture of isoLG-modified PEs with different molecular weights in which the amount of each species could be lower than the lowest limit of mass spectrometric detection. To overcome this problem, we converted the putative complex mixture of isoLG-modified PEs into a much simpler mixture by $PLA_2$-catalyzed selective hydrolysis of the sn-2 acyl, releasing 2-lysophospholipids. To prevent in vitro oxidation, the presence of a transition metal ion chelator (EDTA) was essential at all stages of sample processing. Even in the presence of an excess of $Ca^{2+}$, required by the enzyme $PLA_2$, EDTA remains an effective chelator of transition metal ions because the stability constants for their EDTA complexes, e.g., log K=18.8 or 25.1 for $Cu^{2+}$ or $Fe^{3+}$, are much greater than that of $Ca^{2+}$, i.e., log K=10.7.

Figure 6:
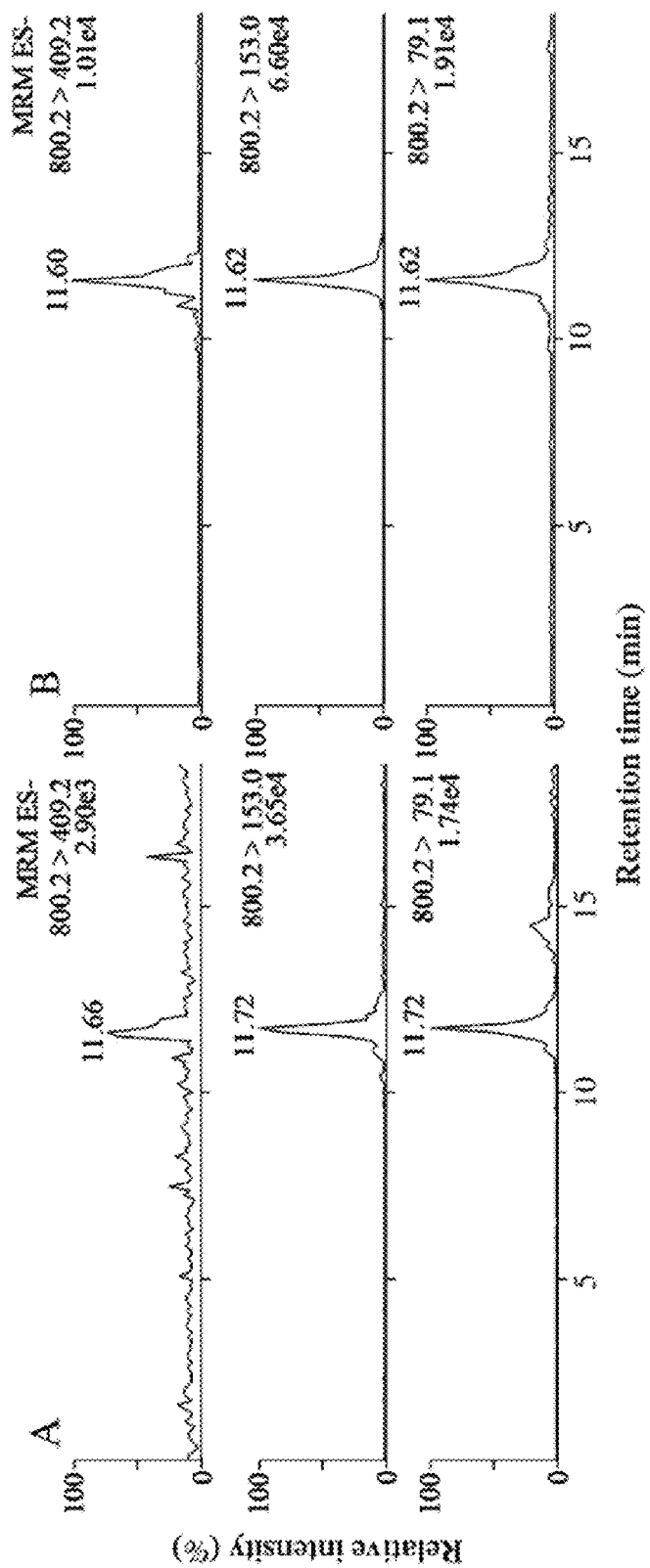
FIG. 6 are histograms illustrating LC/ESI/MS/MS analysis of isoLG-lysoPE-HL adducts derived from human plasma samples. (A) Putative isoLG-lysoPE-HL adducts in lipid extract from human plasma after PLA$_2$ treatment; (B) synthetic standard of iso[4]LGE$_2$-lysoPE-HL adduct was spiked into and then extracted from human plasma without PLA$_2$ treatment, which is required to release endogenous isoLG-lysoPE-HL adducts from their isoLG-PE-HL precursors.

Analysis of a lipid extract from plasma treated with PLA2 revealed the presence of isoLG-lysoPE-HL but not isoLG-lysoPE-lactam (data not shown), confirming that isoLG-PE-HLs are present in vivo. As shown in FIG. 6, the MRM transitions corresponding to all isoLGlysoPE-HL adducts coeluted at a single retention time identical with that of the pure synthetic iso[4]$LGE_2$-lysoPE-HL standard. However, the transitions corresponding to structurally unique fragmentations that are diagnostic for iso[4]$LGE_2$-lysoPE-HL were not detectable. By comparison of the behaviors of putative isoLG-lysoPE-HL and the synthetic standard of iso[4]$LGE_2$-lysoPE-HL in biological matrices, we noticed the absence of diagnostic transitions m/z 800.2→403.9 and 800.2→660.2 corresponding to iso[4]$LGE_2$-lysoPE-HL, as well as the interference from components in the biological sample (matrix effect) in the transition m/z 800.2→255.2 common to all isoLG-lysoPE-HLs. Although they could be detected in the mixture of adducts generated from oxidation of PA-PC in the presence of 2-lysoPE (FIG. 5B) followed by selective hydrolysis with $PLA_2$, neither they nor those expected from the regioisomeric isoLG-lysoPE hydroxylactams could be detected in the mixture of adducts derived from human plasma. These limitations are probably a consequence of the fact that the amount of iso[4]$LGE_2$-lysoPE-HL is only a small portion of the total of all isoLG-lysoPE-HL structural isomers present in vivo. Furthermore, the fragmentation efficiency of the diagnostic transitions for iso[4]$LGE_2$-lysoPE-HL could be suppressed by a matrix effect of components in plasma samples.

Figure 7:
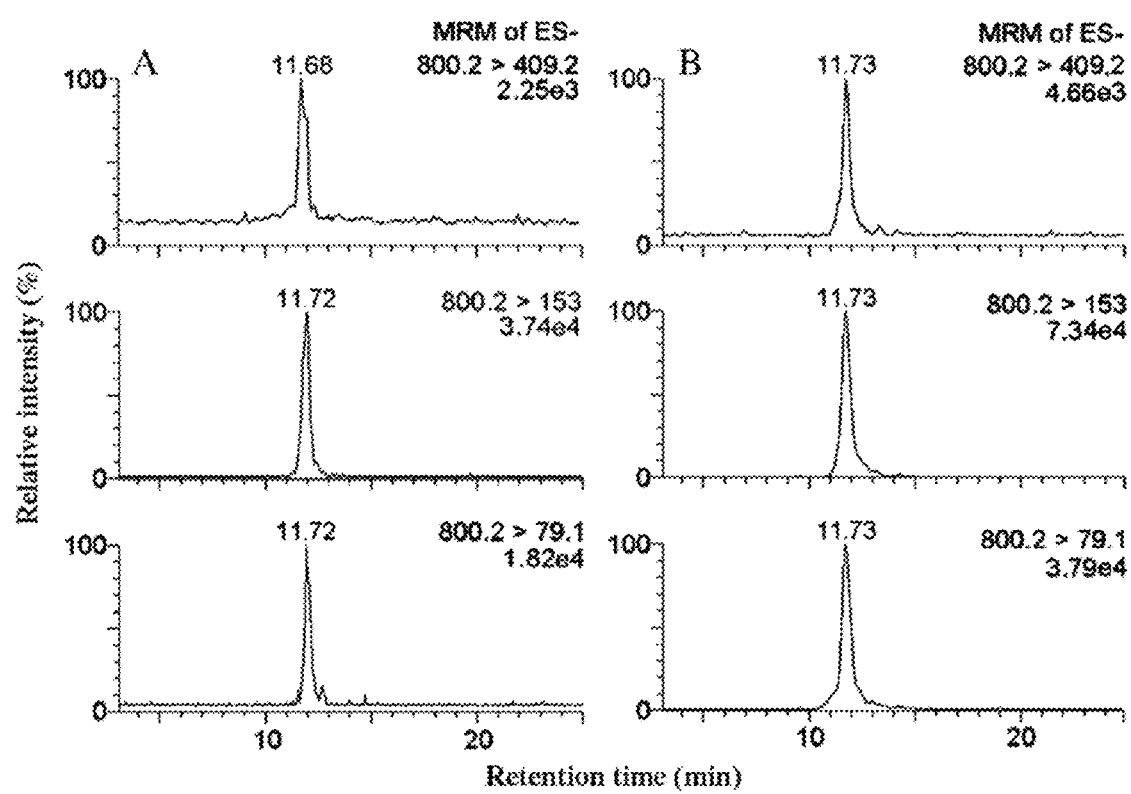
FIG. 7 are histograms illustrating (A) Putative isoLG-lysoPE-HL adducts in lipid extract from human plasma after PLA$_2$ treatment; (B) lipid extract from human plasma after PLA$_2$ treatment—which releases endogenous isoLG-lysoPE-HL adducts from their isoLG-PE-HL precursors—spiked with authentic standard iso[4]LGE$_2$-lysoPE-HL (0.5 ng). The appearance of only single peaks in (B) supports the view that small retention time differences from one HPLC run to another are not evidence for nonidentity with isoLG-lysoPE-HL adducts.

Because small retention time differences are apparent between the peaks attributed to isoLG-lysoPE-HLs in FIGS. 6A and B, we performed a control experiment to confirm that the compounds detected in the plasma sample of FIG. 6A are isoLG-lysoPE-HLs. Thus, a sample of plasma extract, after $PLA_2$ treatment, was spiked with the authentic standard iso [4]$LGE_2$-lysoPE-HL. As shown in FIG. 7, only a single peak was detected in the lipid extract after $PLA_2$ treatment to which was added approximately the same amount of authentic standard (0.5 ng) as there was isoLG-lysoPE-HL presumed to be present in the samples shown in FIG. 7A. Although the total ion current of each scan in FIG. 7B is approximately double those in FIG. 7A, only a single peak is seen in each scan.

Figure 8:
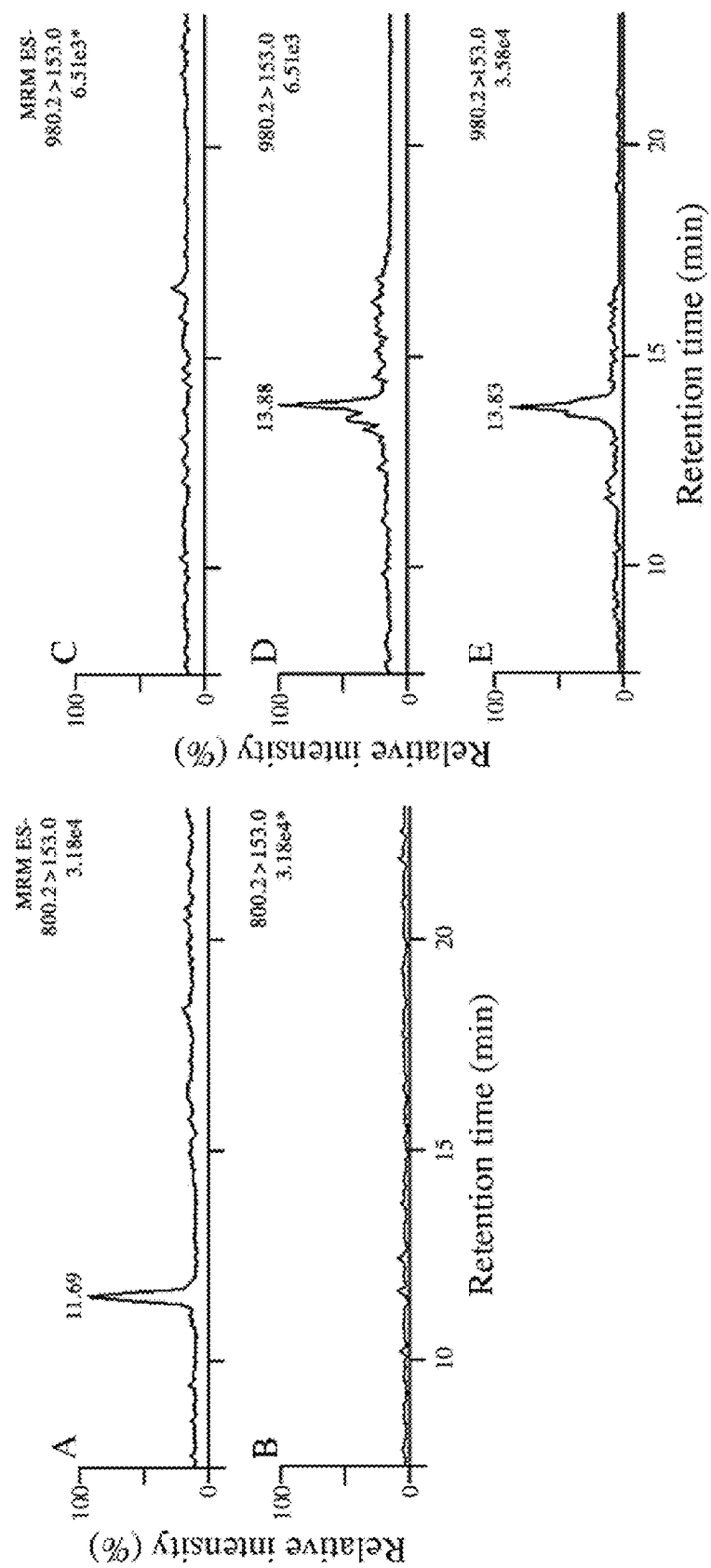
FIG. 8 are histograms illustrating LC/ESI/MS/MS analysis of putative isoLG-lysoPE-HL adducts in plasma extract with PLA$_2$ treatment before and after pentafluorobenzyl (PFB) esterification. (A) MRM for isoLG-lysoPE-HL before PFB derivatization; (B) MRM for isoLG-lysoPE-HL after PFB derivatization; (C) MRM for PFB derivative of isoLG-lysoPE-HL before PFB derivatization; (B) MRM for PFB derivative of isoLG-lysoPE-HL after PFB derivatization; (E) synthetic PFB derivative standard of iso[4]LG-lysoPE-HL adducts. In (B), the intensity of the signal ($3.18 \times 10^4$, with the asterisk) was obtained by normalizing to the intensity of the largest peak in (A) ($3.18 \times 10^4$) from its original intensity $1.05 \times 10^3$. In (C), the intensity of the signal ($6.51 \times 10^3$, with the asterisk) was obtained by normalizing to the intensity of the largest peak in (D) ($6.51 \times 10^3$) from its original intensity $1.26 \times 10^3$. In (A), (D), and (E), the intensities shown are the intensity of the largest peak in each chromatogram. The peak attributed to isoLG-lysoPE-HL disappears upon treatment with PFB-Br and a new peak appears, corresponding to the expected PFB ester.

To further confirm the identity of these in vivo-derived compounds as isoLG-lysoPE-HLs, the lipid extracts from biological samples were treated with a mixture of PFB-Br and diisopropylethylamine to derivatize the carboxylic acid functionality. This introduces a net increase of 180 Da in the molecular weight. The PFB derivative of pure iso[4]$LGE_2$-lysoPE-HLs obtained by chemical synthesis was also prepared as an authentic standard. As shown in FIG. 8, before PFB esterification, no peaks were seen in the MRM transition m/z 980.2→153.0. A peak with the same retention time as the synthetic PFB ester of iso[4]$LGE_2$-lysoPE-HL appears in the channel 980.2→153.0 after esterification. This further confirmed the presence of HL adducts of isoLG-modified PEs in vivo. Furthermore, the peak in MRM transition m/z 800.2→153.0, which represents isoLG-lysoPE-HLs, disappears after esterification (FIG. 8B). Both of these results further confirmed that HL adducts of isoLG-modified PEs are present in vivo.

Figure 9:
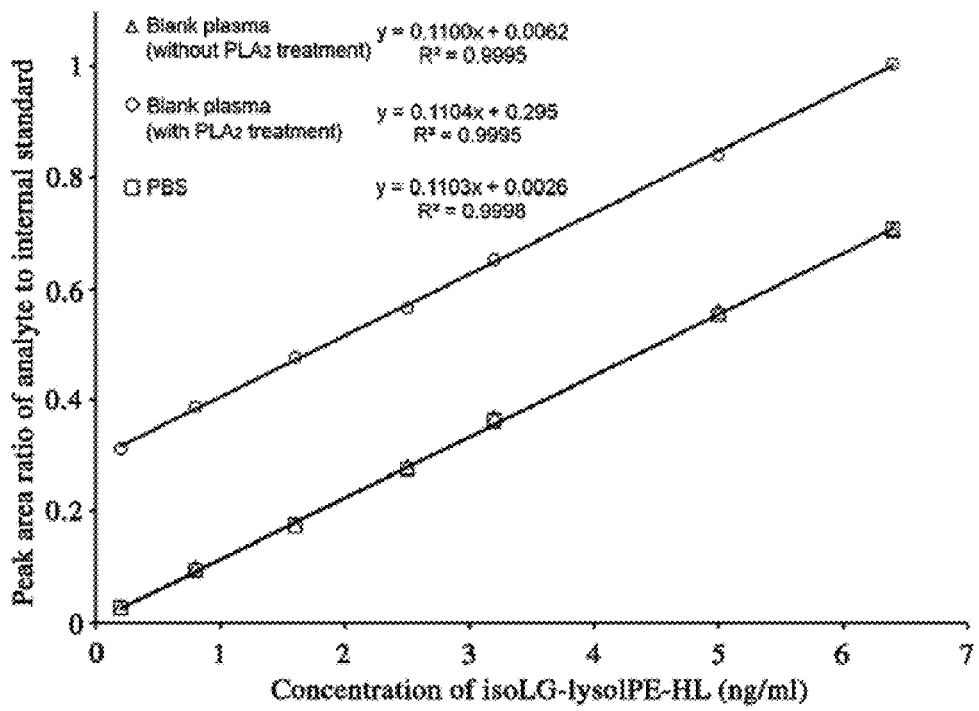
FIG. 9 illustrates calibration curves for iso[4]LGE$_2$-lysoPE-HL in blank plasma without PLA$_2$ treatment, in blank plasma with PLA$_2$ treatment, and in PBS. Data points represent the means of duplicate determinations from a representative experiment performed on three separate occasions. That plasma does not contribute a confounding matrix effect is supported by the superposition of the curves from blank plasma without PLA$_2$ treatment and from PBS. That iso[4]LGE$_2$-lysoPE-HL is released from endogenous lipids in plasma by PLA$_2$ treatment is supported by the elevated non-zero intercept of a parallel calibration curve obtained using plasma with PLA$_2$ treatment.

A calibration curve for iso[4]$LGE_2$-lysoPE-HL was constructed in blank plasma without $PLA_2$ treatment (FIG. 9). We also constructed calibration curves for iso[4]$LGE_2$-lysoPE- HL in blank plasma with $PLA_2$ treatment and in PBS buffer (FIG. 9). The three graphs are parallel straight lines. This supports the view that the isotope-labeled internal standard efficiently minimizes any matrix effect for the biological samples. Moreover, the nonzero y-intercept of the calibration curve constructed for blank plasma with $PLA_2$ treatment confirms the presence of endogenous isoLG-PE-HL in plasma that becomes isoLGlysoPE-HL upon treatment with $PLA_2$.

Figure 10:
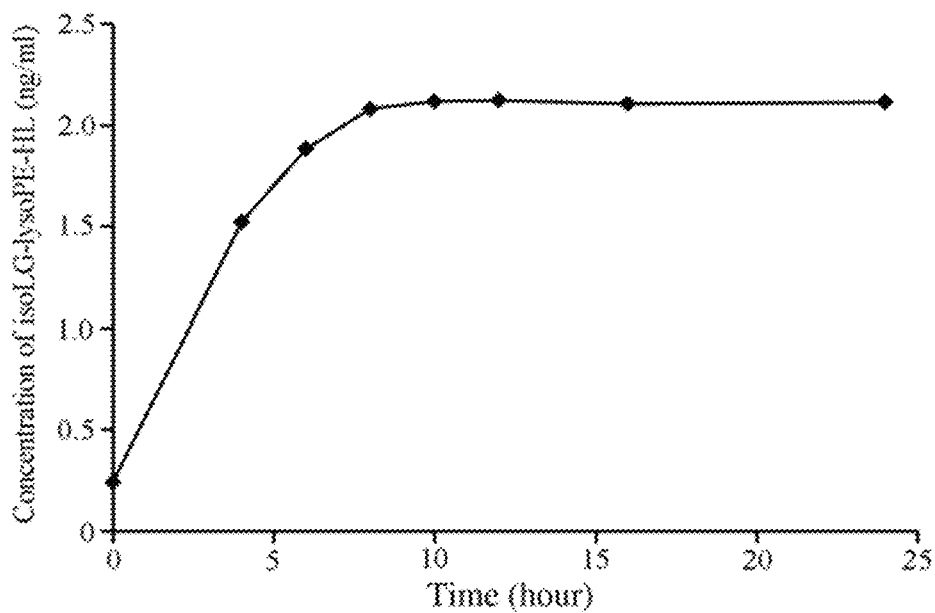
FIG. 10 illustrates a plot of a time course of PLA$_2$-induced generation of isoLG-lysoPE-HL in lipid extracts from human plasma. Data points represent the means of duplicated determinations from a representative experiment performed on three separate occasions. Lipolysis goes to completion by 10 h at 37° C.

Subsequently, we optimized the time for $PLA_2$-catalyzed hydrolysis of plasma lipid extracts. FIG. 10 shows the evolution profiles and maximum and final levels for isoLG-lysoPE-HL produced upon PLA2 hydrolysis of a lipid extract. The level of isoLG-lysoPE-HL in the sample reaches a maximum (plateau) after incubation for 10 h at 37° C.

Replicate analyses of different plasma samples (n=5, Table 1) as well as plasma samples spiked with known amounts of pure iso[4]$LGE_2$-lysoPE-HLs (Table 2) were conducted. The results show that our quantitative method has excellent precision and accuracy.

TABLE 1

Replicated analysis of various plasma samples with $PLA_2$ treatment

| Plasma Sample | Calculated concentration (ng/ml) (mean ± SD) | Intraday CV (%) | Interday CV (%) |
|---|---|---|---|
| C1 | 2.76 ± 0.13 | 3.13 | 4.71 |
| C2 | 3.79 ± 0.21 | 2.15 | 5.54 |
| C3 | 3.44 ± 0.18 | 2.32 | 5.23 |
| C4 | 3.12 ± 0.16 | 2.85 | 5.13 |
| C5 | 2.66 ± 0.14 | 2.65 | 5.26 |

Control samples and AMD study, n = 5. Data points represent the means of duplicated determinations from a representative experiment performed on three separate occasions.

TABLE 2

Blank plasma samples (n = 5) spiked with known amounts (2.5 or 5 ng/ml) of iso[4]$LGE_2$-lysoPE-HL)

| Nominal concentration (ng/ml) | Calculated concentration (ng/ml) (mean ± SD) | Intraday CV (%) | Interday CV (%) | Accuracy (%) |
|---|---|---|---|---|
| 2.5 | 2.45 ± 0.11 | 2.12 | 4.49 | −2.00 |
| 5.0 | 4.88 ± 0.26 | 3.15 | 5.32 | −2.40 |

Addition of PLA2 and CaCl2 during PLA2 treatment was omitted to avoid the generation of additional isoLG-lysoPE-HLs from endogenous phospholipids in plasma. Interday study was conducted in 3 days. Data points represent the means of duplicated determinations from a representative experiment performed on three separate occasions.

In theory, two compounds that are isobaric with 2-lysoPE, i.e., the ether lipid C17:0e/C18:0-glyeroPE or the plasmalogen C17:0p:C16:0-glyceroPE, could interfere with our assay. However, the vast majority of natural fatty acids have an even number of carbon atoms because their biosynthesis involves oligomerization of the two-carbon synthon acetyl-CoA. Alkyl or alkenyl chains with 17 carbons are not major constituents of natural lipids, and such C17 phosphatidylethanolamine derivatives are rare in vivo. It is highly unlikely that such putative naturally occurring isobaric compounds interfere with the assay of isoLG-lysoPE-HLs.

IsoLG-lysoPE-HLs can Provide a Sensitive LC-MS/MS Marker of Oxidative Injury

Our previous studies showed that iso[4]LG-protein adduct levels provide a unique dosimeter of oxidative injury. We found that plasma levels of isoLG-protein adducts are significantly elevated in patients with atherosclerosis or end-stage renal disease compared to normal individuals. We also found significant elevations in the levels of these markers of oxidative injury in patients with cardiovascular disease who had undergone coronary artery bypass surgery. Especially noteworthy was the observation that levels of cholesterol in these patients were significantly lower than those in younger healthy individuals. Presumably, dietary or medicinal interventions were successfully lowering the levels of cholesterol in the cardiovascular disease patients, but levels of oxidative injury, perhaps an indication of chronic inflammation, remained high. Because elevated oxidative injury in these patients may have pathological significance, a sensitive and efficient method is needed to monitor the efficacy of therapeutic interventions. Unfortunately, MS methodology for measuring protein-bound LGs/isoLGs requires large sample sizes, e.g., 2 ml of plasma, and timeconsuming sample preparation to excise LG/isoLG-modified lysine from proteins. Especially notable are the facts that (1) the LG/isoLG-PE-HLs are detectable in biological samples that are an order of magnitude smaller and (2) sample processing is much simpler and less time consuming than required for detecting the corresponding LG/isoLG-lysyl lactams. Both features enhance the potential clinical utility of LG/isoLG-PE-HLs compared to the protein-derived lysyl lactam analogs.

Liver isoLG-PE-HL Adduct Levels are Elevated in Chronic Ethanol-Fed Mice

Mounting evidence over the past decade indicates that reactive oxygen species (ROS) play a critical role in ethanol-induced liver injury. ROS can also induce cyclooxygenation of polyunsaturated fatty acids to form various γ-ketoaldehydes, including $LGE_2$ and iso[4]$LGE_2$. We hypothesized that ethanol exposure induces formation of LGs/isoLGs, which subsequently modify phosphatidylethanolamines resulting in increased levels of isoLG-PE-HL in the liver of a murine model of alcoholic liver disease.

Figure 11:
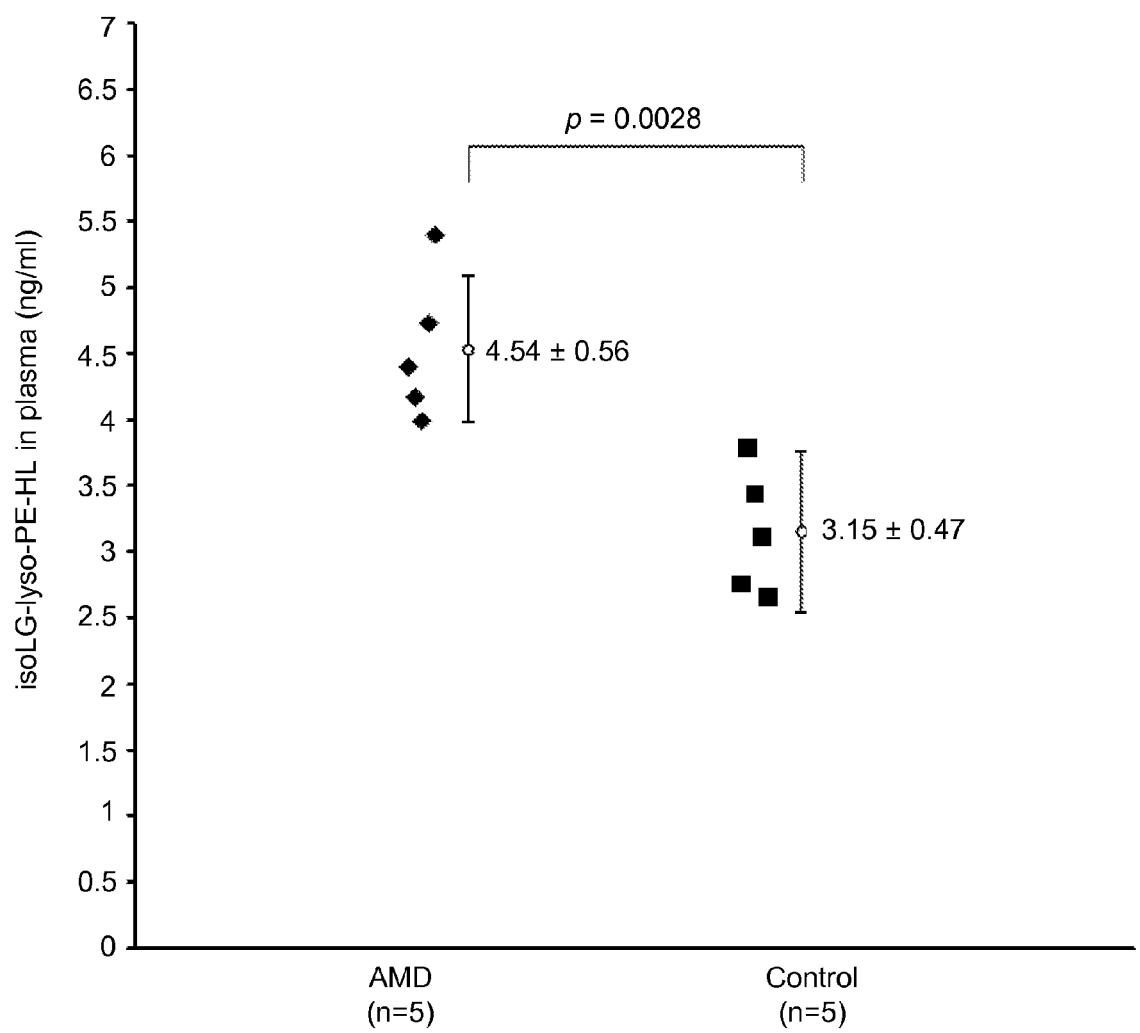
FIG. 11 illustrates levels of isoLG-lysoPE-hydroxylactam adducts in mouse liver using LC-MS/MS. Liver samples were obtained from chronic ethanol (27% of calories for 4 weeks)-fed mice (C57BL/6 female, n=6) and from mice pair-fed diets that isocalorically substituted maltose dextrins for ethanol (n=4). Twofold higher levels (P=0.00021) were detected in livers from chronic ethanol-fed mice (32.4±6.3 ng/g) compared to those of pair-fed mice (12.1±1.5 ng/g).

In an in vivo study (see Example 2), we compared the levels of isoLG-lysoPE-HL adducts in livers from chronic ethanol (27% of calories for 4 weeks)-fed mice (n=6) with those of control animals (n=4, pair-fed diets that isocalorically substituted maltose dextrins for ethanol) by LC-MS/MS after selective phospholipolysis with PLA2 (FIG. 11). Twofold higher levels (P=0.00021) were detected in livers from chronic ethanol-fed mice (32.4±6.3 ng/g) compared to those of pair-fed mice (12.1±1.5 ng/g). Our results confirmed that ethanol exposure enhanced the formation of isoLGs and the derived isoLG-PE-HLs in mouse liver.

Plasma isoLG-lysoPE-HL Levels are Elevated in Age-Related Macular Degeneration

There is growing consensus that age-related macular degeneration is an age-related inflammatory disease triggered in part by oxidative stress. A host of oxidative protein and DNA modifications has been detected at elevated levels in human age-related macular degeneration tissues, including in plasma carboxyethylpyrrole, an oxidative protein modification generated from docosahexaenoatecontaining phospholipids, and carboxymethyllysine and pentosidine, oxidative protein modifications generated from sugars through the Maillard reaction. We hypothesized that chronic inflammation in age-related macular degeneration patients would result in elevated plasma levels of isoLG-PE adducts. In a pilot clinical study, we compared isoLG-lysoPE-HL levels in plasma from age-related macular degeneration and age- and gender-matched control subjects (FIG. 12). The mean level detected in age-related macular degeneration plasma (5.2±0.4 ng/ml, n=15 patients) was significantly elevated (P b 0.0001) compared with plasma from healthy volunteers (3.4±0.1 ng/ml, n=15). Our preliminary results support the potential utility of these ethanolamine phospholipid adducts as biomarkers for detecting risk to diseases stimulated by oxidative stress. The results also reinforce the association between oxidative stress and age-related macular degeneration and are consistent with the hypothesis that agerelated macular degeneration is a systemic disease. A much larger clinical study is now warranted, including evaluation of the possibility that isoLG-lysoPE-HL plasma levels, in combination with other biomarkers, may enhance prognostic utility. For example, we recently demonstrated that for individuals exhibiting elevated carboxyethylpyrrole marker levels, the risk for age-related macular degeneration was increased approximately two- to threefold relative to that predicted by age-related macular degeneration risk genotype alone. This study showed that combined carboxyethylpyrrole proteomic and genomic biomarker measurements are more effective in predicting age-related macular degeneration risk than either method alone. Other recent proteomic studies suggest that plasma protein levels of carboxymethyllysine together with pentosidine discriminate between age-related macular degeneration and control patients with 89% accuracy and that pentosidine in combination with carboxyethylpyrrole adducts can discriminate with 92% accuracy. Thus, isoLG-lysoPE-HL measurements in combination with other biomarkers may improve methods for disease prognosis and for monitoring therapeutic efficacy.

Biological Significance of PE Modification by LGs or isoLGs

Oxidatively damaged LDL accumulates in atherosclerotic plaques owing to endocytosis by monocyte macrophages in the subendothelial space. Because ethanolamine phospholipids constitute only a few percent of total LDL phospholipids, their physiological roles may be especially susceptible to interference by covalent modification, which may also generate pathological new activities. The accumulation of aldehyde-modified PEs in atherosclerotic lesions but not in circulating LDL suggests an atherogenic role. Covalent modification of the primary amino group in LDL PEs by aldehydes was postulated to contribute to prothrombotic activity involving stimulation of platelet prothrombinase activity.

In addition to their potential as clinically useful dosimeters of oxidative injury, the present demonstration of the presence of LG/isoLG-modified ethanolamine phospholipids in vivo may have pathological significance arising from the effects of these modifications on membrane function. Ethanolamine phospholipids account for 27-52% of the total phospholipids in brain (52% in myelin white matter), heart, liver, kidney, spleen, erythrocytes, and platelets. Because PE prefers to organize itself into nonbilayer structures, it is noteworthy that biomembranes contain a substantial amount of this nonbilayer lipid. The fact that levels of nonbilayer lipids are precisely regulated implies "that they are of considerable functional importance". Apparently, the biological activity of some membrane proteins, such as transporters, depends on the presence of PE, because its depletion causes a loss of activity, which is restored upon replacing the PE. Therefore, modifications of ethanolamine phospholipids by covalent adduction of their primary amino residues with lipid oxidation products could compromise membrane function, e.g., by impairing their ability to stabilize membrane proteins. Membrane structure and the interactions of membrane PEs with membrane-bound or cytosolic proteins may be profoundly altered by the conversion of the positively charged amino group of the PEs into a negatively charged group upon conversion to LG/isoLG-PE-HL derivatives. Modifications of ethanolamine phospholipids may be of mechanistic significance for the loss of blood-brain barrier integrity that we detected as a consequence of injecting minute quantities of $LGE_2$ into rat brain.

Mitochondrial membrane is especially vulnerable to oxidative damage because various free radical species are generated by components of the electron transport chain in the membrane during mitochondrial respiration. Modification of PE by lipid oxidation products, such as 4-HNE, was proposed to account for the formation of fluorescent chromolipids upon oxidation of rat liver microsomes or mitochondria, and covalent modification by lipid peroxidation products was shown to alter membrane fluidity. The possible contribution of LGs/isoLGs to the production of such chromolipids merits investigation.

Reaction of LGs/isoLGs with proteins generates protein-protein crosslinks orders of magnitude more rapidly than other products of lipid oxidation, e.g., MDA. Interestingly, MDA accumulation disturbs the organization of ethanolamine phospholipids in the human erythrocyte membrane, and it was suggested that this might be a consequence of crosslinking by MDA. Covalent adduction of LGs or isoLGs with PEs is not only expected to cause PE-PE crosslinking analogous to their ability to generate protein-protein crosslinks, but also could crosslink proteins with phospholipids resulting in anchoring of proteins to membranes.

EXAMPLE 2

TNF-α plays a central role in alcoholic liver disease. Several reports indicate that elevated levels of circulating endotoxins, increased production of hepatic TNF-α and ROS work in concert during ethanol-induced liver injury. Ethanol-induced ROS has been reported to sensitize the hepatocytes to TNF-α-induced toxicity. Animals deficient in TNF-α receptor 1 (TNFR1) or receiving TNF-α antibody are protected from ethanol induced liver injury. Here, we hypothesize that ethanol feeding induces TNF-α-mediated ROS generation via TNFR1-signalling subsequently elicit peroxidation of lipids and tissue injury.

To test our hypothesis, we measured protein adducts of novel oxidized lipids, $LGE_2$- and iso[4]$LGE_2$, as the new markers of oxidative stress in the liver of wild type mouse (C57BL6) as well as in COX-1, COX-2 or TNFR1 deficient mice following ethanol feeding. Our results showed that the formation of $LGE_2$, iso[4]$LGE_2$- and 4-HNE-protein adducts in mouse liver in response to ethanol feeding was independent of COX-1 or 2, but TNFR1 dependent.

Materials and Methods

Materials

Female C57BL/6 mice (8-10 weeks old) were purchased from Jackson Labs (Bar Harbor, Me.). Lieber-DeCarli high-fat ethanol and control diets were purchased from Dyets (Bethlehem, Pa.). Female COX-1 (strain B6; 129P2Ptgs1$^{tm1Unc}$) or COX-2 (strain B6; 129P2Ptgs2$^{tm1Sm1}$)-knock out mice and their wild types were purchased from Taconic Farms (Germantown, N.Y.). Female TNFR1 (strain B6; 129/Tnfrsfla$^{tm1Imak/J}$) knock out mice were purchased from The Jackson Laboratory (Bar Harbor, Me.).

Antibodies were from the following sources: CYP2E1 (Research Diagnostics, Inc., Flanders, N.J.), 4-HNE-antiserum (Alpha Diagnostics, San Antonio, Tex.) and TNF-α (R&D Systems, Minneapolis, Minn.). Alexa fluor-488 conjugated secondary antibodies were purchased from Invitrogen (Carlsbad, Calif.). Anti-iso[4]$LGE_2$ and $LGE_2$ antibodies have been previously characterized.

Ethanol Feeding

All procedures using animals were approved by the Cleveland Clinic Foundation Institutional Animal Care and Use Committees. Mice were housed in shoe-box cages (2 animals/cage) with microisolator lids. Standard microisolator handling procedures were used throughout the study. Mice were randomized into ethanol-fed and pair-fed groups and then adapted to control liquid diet for 2 days. The ethanol-fed group was allowed free access to ethanol containing diet with increasing concentrations of ethanol: 1% (vol/vol) and 2% each for 2 days, then 4% ethanol for 7 d, and finally 5% ethanol for a further 4 weeks. For the dose-response experiment, mice were allowed free access to 1% ethanol for 2 days and then 2%, 4% or 6% ethanol for a further 2 days. Control mice were pair-fed diets which iso-calorically substituted maltose dextrins for ethanol over the entire feeding period. Mice were then anesthetized, blood samples taken into non-heparinized syringes from the posterior vena cava, livers blanched with saline via the portal vein and then excised. Portions of each liver were then either fixed in formalin or frozen in optimal cutting temperature (OCT) compound (Sakura Finetek U.S.A., Inc., Torrance Calif.) for histology, frozen in RNAlater (Qiagen, Valencia, Calif.) or flash frozen in liquid nitrogen and stored at −80° C. until further analysis. Blood was transferred to heparin-containing tubes for the isolation of plasma. Plasma was then stored at −80° C.

Plasma ALT Measurement

Plasma samples were assayed for alanine aminotransferase (ALT) using a commercially available enzymatic assay kit (Diagnostic Chemicals, LTD, Oxford, Conn.) following the manufacturer's instructions.

Liver Histology and Triglycerides

Formalin-fixed tissues were paraffin embedded, sectioned and stained with hematoxylin and eosin. Sections were coded prior to analysis and examined by two independent individuals. For Oil Red O staining, 10 micron sections were cut from frozen OCT samples and affixed to a microscope slide. Slides were then stored at 4° C. until staining. Liver sections were then air dried for 5-10 min at room temperature and stained in fresh Oil Red O (Sigma, St. Louis, Mo.) for 12 minutes, rinsed in water and then counterstained with hematoxylin. Total liver triglycerides were measured using the Triglyceride Reagent Kit from Pointe Scientific Inc. (Lincoln Park, Mich.).

Immunohistochemistry

Formalin-fixed paraffin embedded liver sections were de-paraffinized in Safeclear II xylene substitute (Protocol, Kalamazoo, Mich.), (3 times 3 min each) and hydrated consecutively in 100% (2 times), 70% and 30% ethanol followed by two washes in PBS. Sections were then blocked with PBS containing 2% BSA, 1% fish gelatin and 0.1% Triton-X-100 for 1 hr and incubated overnight with polyclonal rabbit anti-4-HNE antibody or iso-4-LGE$_2$ or LGE$_2$ anti-sera (diluted 1:250 in blocking buffer) at 4° C. in a moist, chamber. After three washes in PBS (3 times 5 min each), sections were then incubated with the fluorochrome-conjugated secondary antibody (Alexa fluor-488 labeled goat-anti-rat IgG, 1:250 diluted in blocking buffer) for 2 hr at room temperature. Sections were then washed three times in PBS and mounted with VECTASHIELD containing anti-fade reagent (Vector Laboratories, Inc., Burlingame, Calif.). Fluorescence images were acquired using a LEICA confocal microscope. No specific immunostaining was seen in sections incubated with PBS rather than the primary antibody. Images were analyzed and semi-quantitated using Image pro software.

Liver Homogenization 0.5-1.0 g of frozen liver tissue was homogenized in 10 ml/g tissue in lysis buffer (50 mM Tris-HCl, pH7.4, 1% NP-40, 0.25% Na-deoxycholate, 150 mM NaCl, 1 mM EDTA with added protease inhibitors Complete™ (Roche Diagnostics, Mannheim, Germany), 17.5 µg/ml aprotinin, 5 µg/ml bestatin, 10 µg/ml leupeptin, 1 mg/ml bacitracin, and 20 µg/ml E64) and phosphatase inhibitors (1 mM vanadate and 10 mM Na pyrophosphate)) using 15 strokes in a glass on glass homogenizer (loose pestle). After 15 min on ice, samples were centrifuged at 16,000×g for 15 min to remove insoluble material. Protein concentrations were measured. Samples were then used to measure hepatic cytokine concentrations (see below) or normalized and samples prepared in Laemmli buffer and boiled for 5 min. Samples were then separated by SDS-polyacrylamide gel electrophoresis and transferred to membranes for Western blotting. Membranes were probed with specific antibodies against CYP2E1 overnight at 4° C., then washed and incubated for 1 h in secondary antibodies coupled to horseradish peroxidase. Bound antibody was detected by chemiluminescence. Immunoreactive protein quantity was assessed by scanning densitometry.

ELISA for iso[4]LGE$_2$

ELISA for iso[4]LGE$_2$ was performed as suggested in U.S. Pat. No. 5,686,250. Liver homogenates were prepared as described except that 50 µM butylated hydroxytoluene (BHT) and 100 µM diethylenetriamine pentaacetic acid (DTPA) were added to the buffer to prevent aerial oxidation of lipids during homogenization. 50 µg of protein was used in the ELISA.

Liquid Chromatography-Mass Spectrometry Analysis

Liquid chromatography-mass spectrometry analysis for iso[4]LGE$_2$-PE Detection of iso[4]LGE$_2$-PE was carried out according to Example 1.

Statistical Analysis

Values reported are means±SEM. Because of the logistics of animal care, several feeding trials were carried out and combined for the final data analysis. Data were analyzed by general linear models procedure (SAS, Carey, Ind.). Data were log transformed if needed to obtain a normal distribution. Follow-up comparisons were made by least square means testing.

Results

Here we have utilized both long-term (chronic) and short-term models of ethanol exposure. In the chronic model, mice were allowed free access to increasing concentrations of ethanol for 39 days. Neutral lipid was accumulated gradually in the liver during this period ranging from microvesicular lipid droplets at 4% d3 to the macrovesicular droplets by 5% wk 4 (FIG. 13A). In this model of ethanol feeding, plasma ALT, a measure of hepatocyte injury, increased gradually following ethanol exposure starting from 4% d3, matching the pattern of hepatic triglyceride accumulation. In the short-term model of ethanol exposure, mice were exposed to increasing concentrations of ethanol for 2 days. Hepatic triglycerides, assessed by Oil Red O staining, increased at the higher doses (4 and 6%) of ethanol feeding (FIG. 13B). Quantitative measurements of hepatic triglycerides as well as plasma ALT also increased at 4 and 6% (FIG. 14). CYP2E1, one of the major ethanol metabolizing enzymes in liver, plays a critical role in ethanol-induced hepatic injury. Hepatic CYP2E1 was increased over time in response to chronic ethanol feeding reaching a maximum at 5% wk 2 followed by a sustained induction during the remaining feeding period (FIG. 15).

Figure 16:
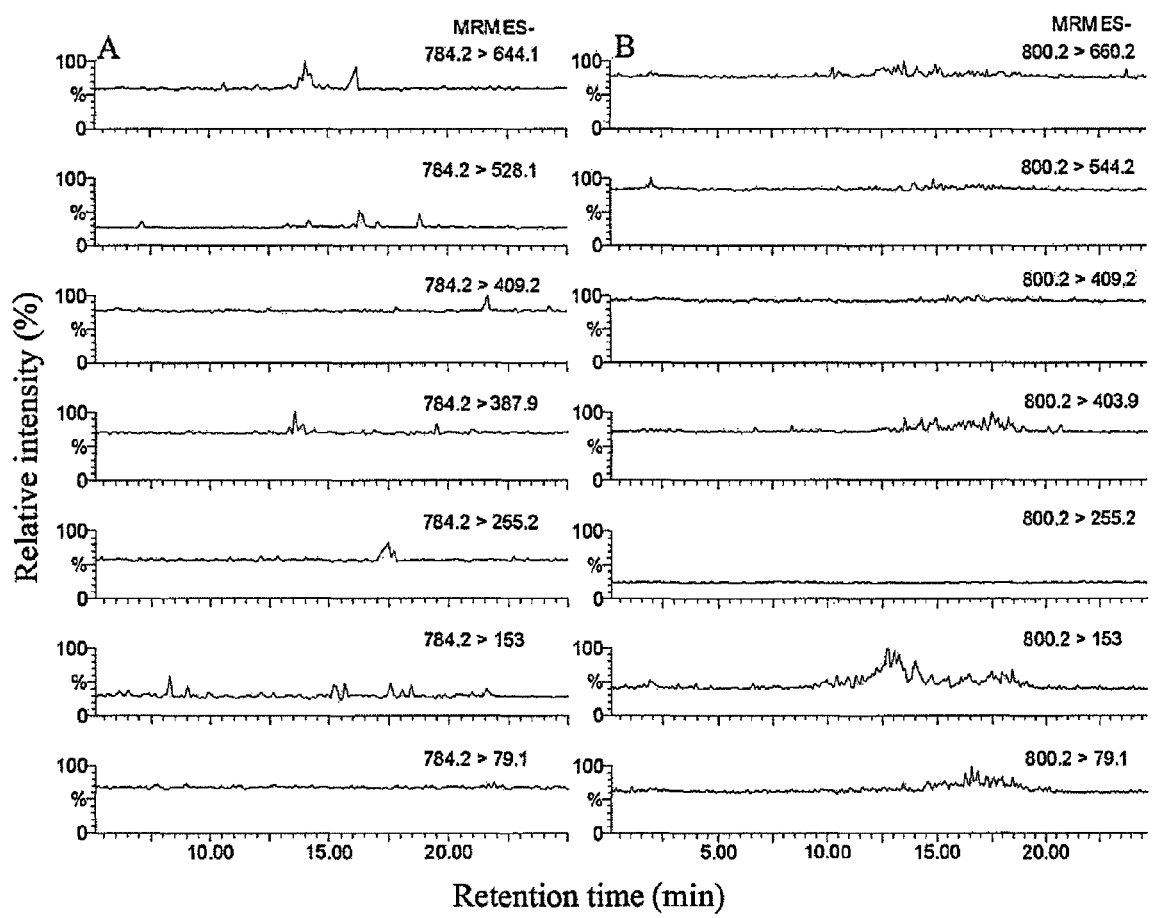
FIG. 16 illustrates increased iso[4]LGE$_2$, LGE$_2$ or 4-HNE-protein adducts in mouse liver after chronic ethanol exposure. Mice allowed free access to increasing concentrations of ethanol-containing diets or pair-fed control diets for 39 days (5% wk 4). A) Paraffin-embedded livers were de-paraffinazied followed by immuno-detection of respective aldehyde-protein adducts using immunofluorescence. All images were acquired using 40× objective. Figures are representative of 2-4 images per liver and at least 3 mice per experimental condition. B) ELISA for iso[4]LGE$_2$ or C) LC-MS analysis for phosphoethanolamine adducts in mouse liver after chronic ethanol exposure Values represent means±SEM, n=3 to 5, *p<0.05 was considered as significant.
Figure 17:
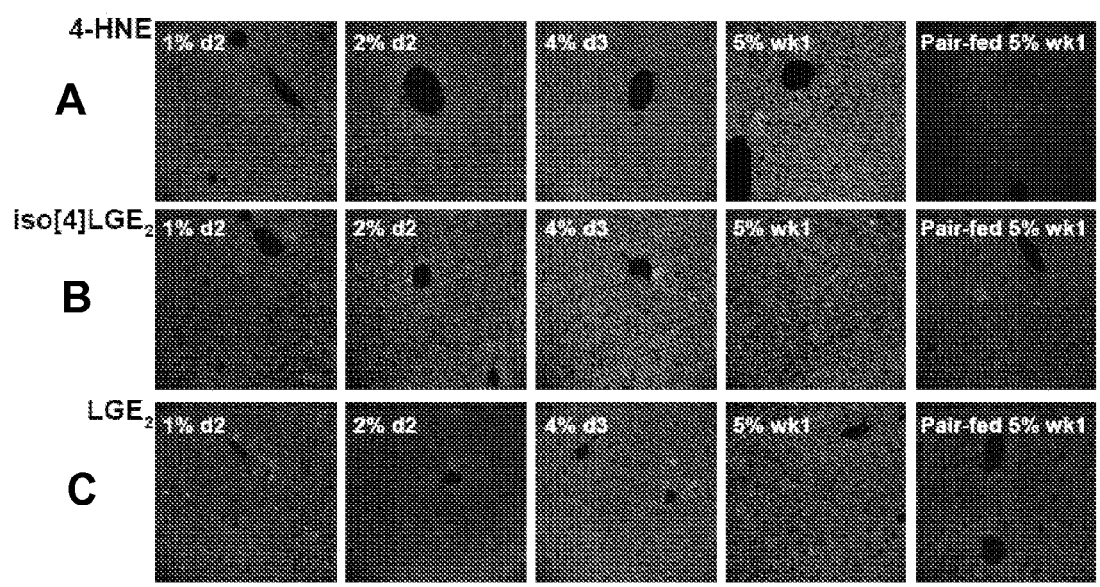
FIG. 17 illustrates time dependent increase of iso-4-LGE$_2$, LGE$_2$ or 4-HNE-protein adducts in mouse liver during chronic ethanol exposure. Mice allowed free access to increasing concentrations of ethanol-containing diets or pair-fed control diets for 2-39 days (5% wk 4). Paraffin-embedded livers were de-paraffinized followed by immuno-detection of A) 4-HNE, B) iso[4]LGE$_2$ or C) LGE$_2$-protein adducts using immunofluorescence. All images were acquired using 40× objective. Figures are representative of 2-4 images per liver and 3 mice per experimental condition.
Figure 18:
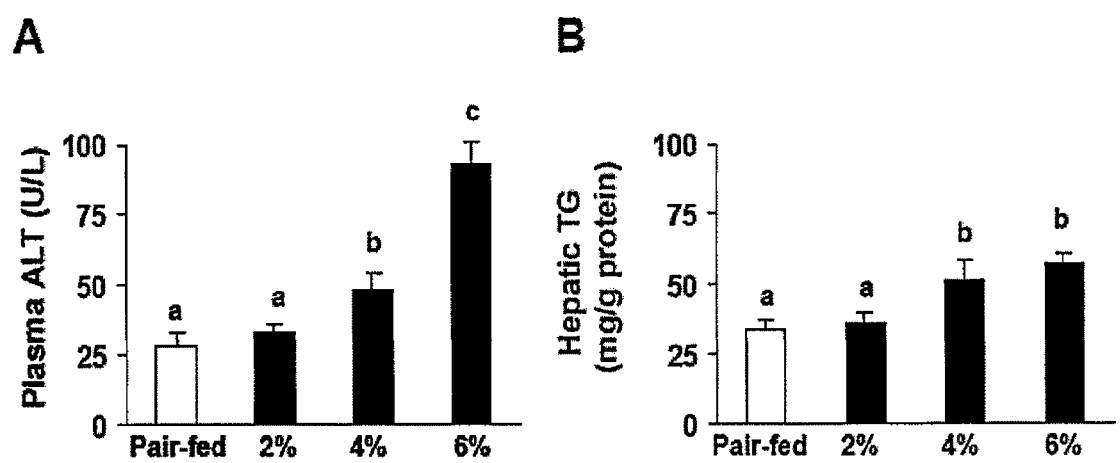
FIG. 18 illustrates ethanol-induced increase of iso-4-LGE$_2$, LGE$_2$ or 4-HNE-protein adducts in mouse liver was dose dependent. Mice allowed free access to 1% ethanol-diet followed by increasing concentrations of ethanol-containing diets (2, 4 or 6%) for 2 days. Control animals received pair-fed diet which iso-calorically substituted with maltose-dextrins for ethanol. Paraffin-embedded livers were de-paraffinazied followed by immuno-detection of 4-HNE, iso[4]LGE$_2$ or LGE$_2$-protein adducts using immunofluorescence. All images were acquired using 40× objective. Figures are representative of 2-4 images per liver and 3 mice per experimental condition.

After chronic ethanol exposure (5% wk 4), protein adducts of different lipid peroxidation products including 4-HNE, LGE$_2$ and iso[4]LGE$_2$ were detected in the liver using immunohistochemistry (FIG. 16A). Adducts were distributed across both periportal and pericentral regions of the liver. Adducts of iso[4]LGE$_2$ were also quantified by ELISA and liquid chromatography-mass spectrometry (LC/MS). Adducts were 2-fold higher in chronic ethanol-fed mouse liver (5% wk 4) compared to the pair-fed animals (FIGS. 4B and 4C). During the course of chronic ethanol feeding, increases in 4-HNE, LGE$_2$ and iso[4]LGE$_2$ adducts were first detectable at 4% d3 (FIG. 17), concurrent with the increase in plasma ALT and hepatic TG. In the short-term model of ethanol exposure, 4-HNE, LGE$_2$ and iso[4]LGE$_2$-protein adducts were increased only at 6% ethanol feeding (FIG. 18), where the increase in plasma ALT and hepatic TG were highest (FIG. 14).

Figure 19:
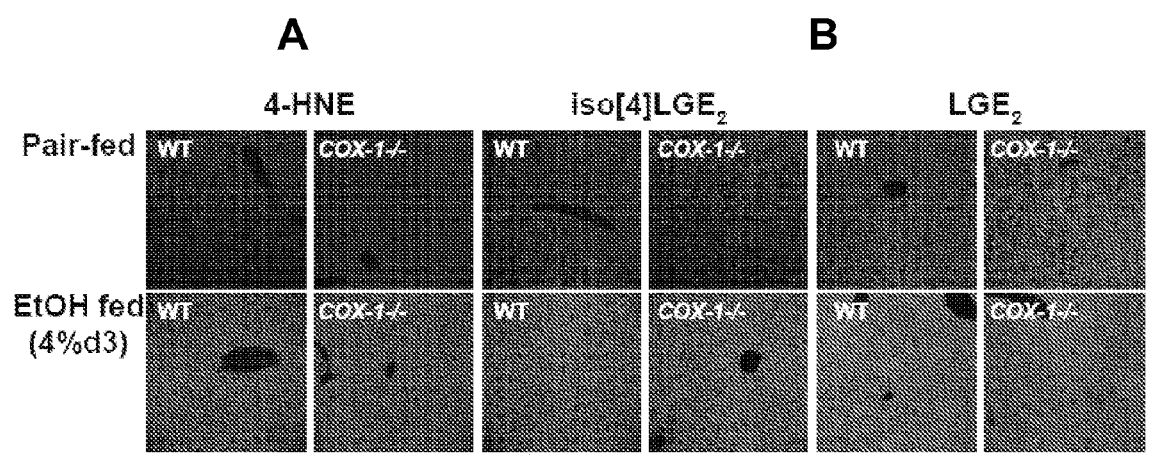
FIG. 19 illustrates ethanol-induced γ-ketoaldehyde-adduct formation in wild type and COX-1-deficient mouse liver. Mice of both strains allowed free access to increasing concentrations of ethanol-containing diets or pair-fed control diets for 7 days (4% d3). Paraffin-embedded livers were de-paraffinized followed by immuno-detection of (A) 4-HNE and (B) iso[4]LGE$_2$-protein adducts using immunofluorescence. All images were acquired using 40× objective. Figures are representative of 2-3 images per liver and 4-6 mice per experimental condition.
Figure 20:
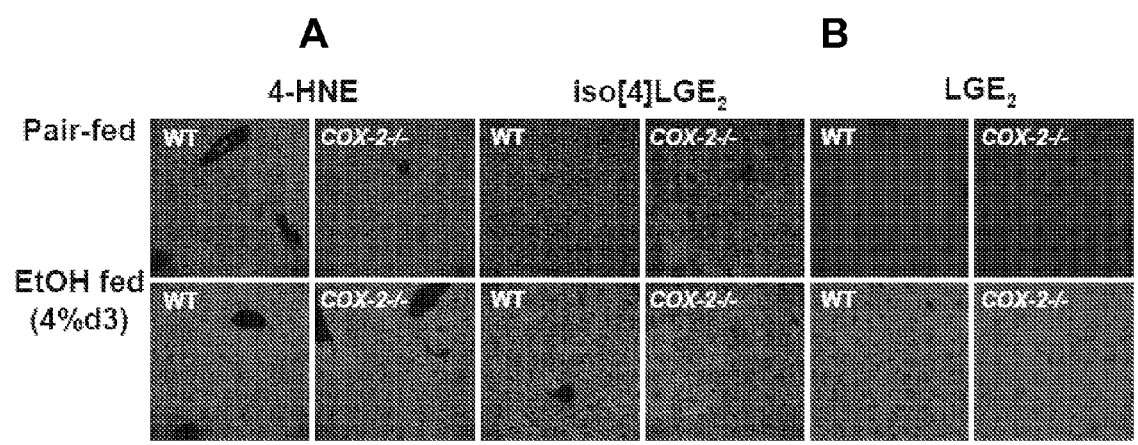
FIG. 20 illustrates ethanol-induced γ-ketoaldehyde-adduct formation in wild type and COX-2-deficient mouse liver. Mice of both strains allowed free access to increasing concentrations of ethanol-containing diets or pair-fed control diets for 7 days (4% d3). Paraffin-embedded livers were de-paraffinized followed by immuno-detection of (A) 4-HNE and (B) iso[4]LGE$_2$-protein adducts using immunofluorescence. All images were acquired using 40× objective. Figures are representative of 2-3 images per liver and 4-6 mice per experimental condition.

We next investigated the mechanism of ethanol-induced γ-ketoaldehyde-adduct formation including LGE$_2$ and iso[4] LGE$_2$ using immunohistochemistry. If formation of LGE$_2$ and iso[4]LGE$_2$ was dependent on cyclooxygenase activity, adduct formation would be reduced in the liver of COX-1 or COX-2-deficient mice in response to ethanol feeding. Ethanol feeding increased LGE$_2$ and iso[4]LGE$_2$-protein adducts in both wild type and COX-1 or 2 deficient mouse liver (FIGS. 19 and 20). These data exclude a role for both cyclooxygenase isozymes, COX-1 and COX-2 in ethanol-mediated LGE$_2$ and iso[4]LGE$_2$-protein adducts formation.

Figure 21:
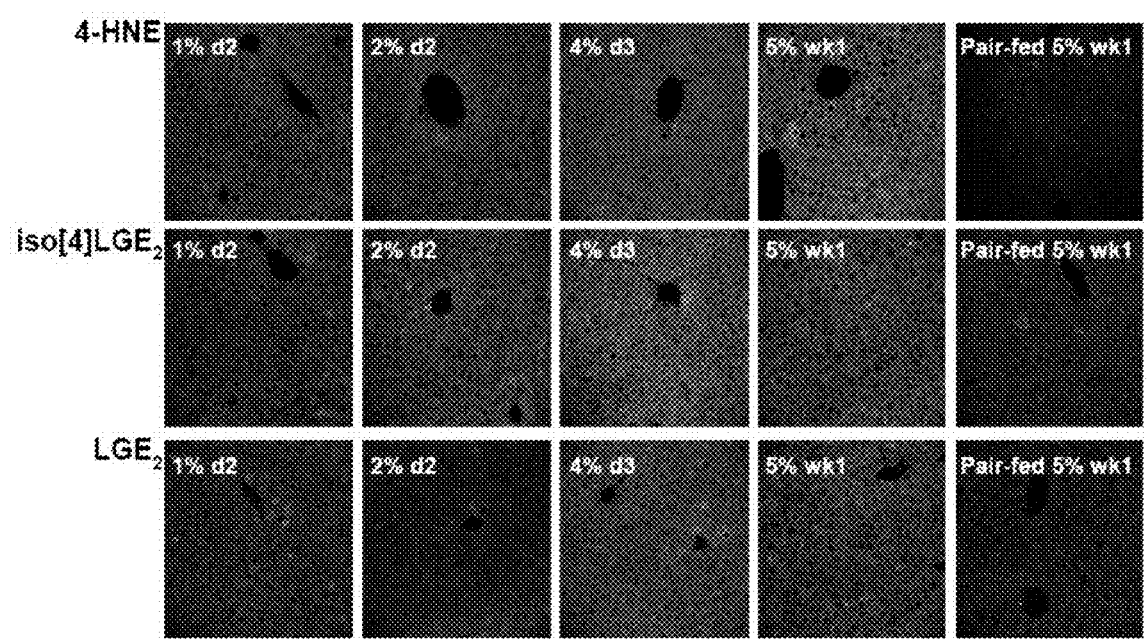
FIG. 21 illustrates time dependent increase of TNF-α in mouse liver during chronic ethanol exposure. Mice allowed free access to increasing concentrations of ethanol-containing diets or pair-fed control diets for 2 to 39 days. Optimal cutting temperature-embedded mouse livers subjected to immuno-detection for TNF-α using immunofluorescence. All images were acquired using 40× objective. Figures are representative of 2-3 images per liver and 3 mice per experimental condition.
Figure 22:
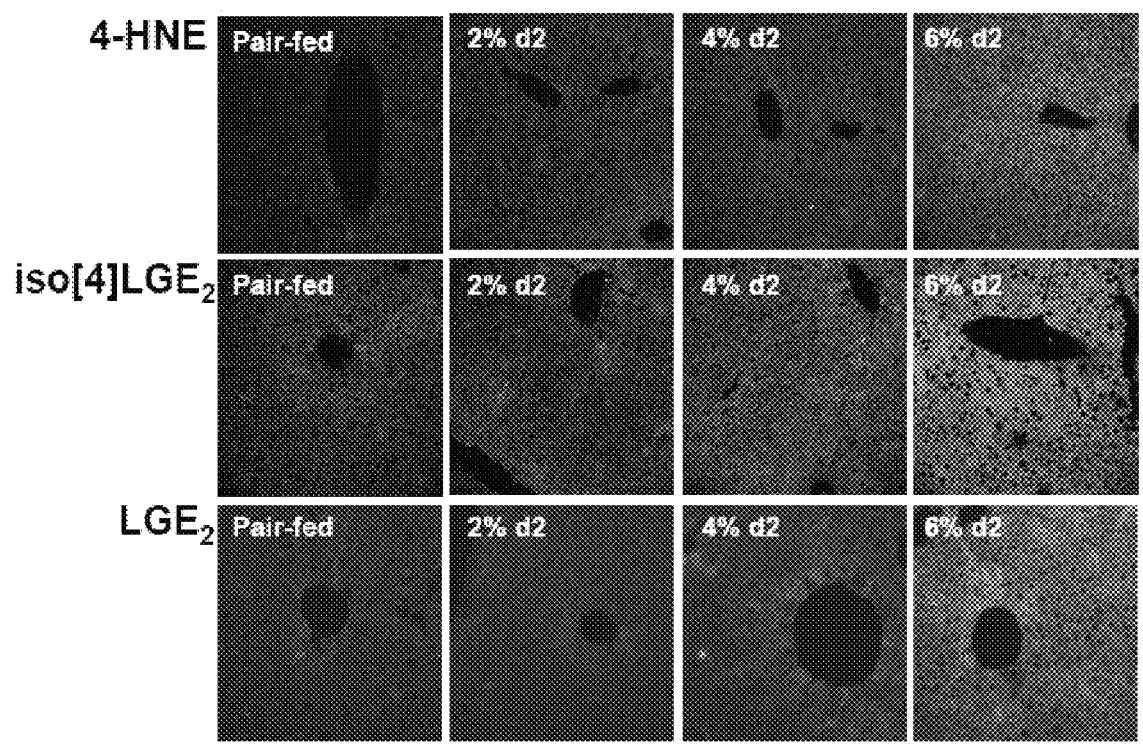
FIG. 22 illustrates TNF-R1 deficiency prevented ethanol-induced γ-ketoaldehyde-adduct formation. Mice of both strains allowed free access to increasing concentrations of ethanol-containing diets or pair-fed control diets for 11 days (4% d7). Paraffin-embedded livers were de-paraffinized followed by immuno-detection of (A) 4-HNE and (B) iso[4]LGE$_2$-protein adducts using immunofluorescence. All images were acquired using 40× objective. Figures are representative of 2-3 images per liver and 3 mice per experimental condition.

Up-regulation of pro-inflammatory cytokines, including TNF-α, is a key event during ethanol-induced liver injury. We first investigated the time-dependent induction of TNF-α in the liver during long-term ethanol exposure. Long-term ethanol feeding showed a biphasic induction of TNF-α in mouse liver. An early transient peak at 2% d2 was followed by a later peak at 5% wk 4 (FIG. 21). Previous reports indicate that ethanol induced TNF-α can trigger ROS overproduction via mitochondrial respiratory chain dysfunction. Neutralizing the activity of TNF-α, using anti-TNF-α antibody or deficiency of TNFR1, protect mice against ethanol induced liver injury. We therefore hypothesized that TNFR1 deficiency offered protection against ethanol-induced liver injury by restricting the formation of hepatic ROS which subsequently prevents the accumulation of 4-HNE and iso[4]LGE$_2$-protein adducts following ethanol exposure. In agreement with our hypothesis, formation of ethanol-induced (4% d7) 4-HNE and iso[4]LGE$_2$-protein adducts were blunted in TNFR1-deficient mouse livers compared to their wild type counterparts (FIG. 22).

Our results demonstrated that both chronic or short-term ethanol feeding induced the production of protein adducts of reactive γ-ketoaldehydes, LGE$_2$ and iso[4]LGE$_2$ and hydroxyalkenals, 4-HNE in mouse livers. Formation of these lipid peroxidation products was dependent on duration and dose of ethanol exposure. Ethanol-mediated induction of these adducts were co-incident with other pathological markers of liver injury such as plasma ALT and hepatic TG, but occurred after an early spike in inflammatory cytokine, TNF-α. Moreover, formation of these adducts were dependent on TNF-α signaling via TNFR1, but independent of arachidonate metabolizing enzymes, cyclooxygenase 1 and 2.

In summary, we show that ethanol feeding induced the formation of reactive γ-ketoaldehydes in mouse livers, which readily binds with proteins to form stable covalent adducts. Ethanol-induced TNF-α is critical for iso[4]LGE$_2$ protein adduct formation in mouse livers, while arachidonic acid metabolizing enzymes, COX-1 or 2 do not contribute to the formation of γ-ketoaldehyde-adducts. Reactive γ-ketoaldehydes formed in course of ethanol feeding can readily bind to a variety of cellular proteins, resulting in impaired protein function or signaling.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of measuring isolevuglandin and/or levuglandin ethanolamine phospholipid adducts associated with oxidative injury in a subject, the method comprising:
obtaining a bodily sample suspected of including isolevuglandin and/or levuglandin ethanolamine phospholipid adducts from a subject,
selectively hydrolyzing isolevuglandin and/or levuglandin ethanolamine phospholipid adducts from the sample with a phospholipase A2 (PLA2) enzyme that forms isolevuglandin and/or levuglandin 2-lysoethanolamine phospholipid derivatives, and
determining the amount of isolevuglandin and/or levuglandin 2-lysoethanolamine phospholipid derivatives by mass spectrometry, wherein the amount of isolevuglandin and/or levuglandin 2-lysoethanolamine phospholipid derivatives is determinative of the level of isolevuglandin and/or levuglandin ethanolamine phospholipid adducts in the sample and indicative of the level of oxidative injury in the subject, and wherein an increased level of isolevuglandin and/or levuglandin ethanolamine phospholipid adducts in the subject compared to a control level is indicative of an increased level of oxidative injury in the subject.

2. The method of claim 1, wherein the isolevuglandin and/or levuglandin ethanolamine phospholipid adducts are extracted from the bodily sample.

3. The method of claim 2, wherein isolevuglandin and/or levuglandin ethanolamine phospholipid adducts are extracted from the bodily sample in the presence of at least one of a chelating agent or antioxidant to inhibit oxidation of the bodily sample.

4. The method of claim 3, the chelating agent or antioxidant comprising at least one of ethylenediaminetetraacetic acid (EDTA) or butylated hydroxytoluene (BHT).

5. The method of claim 1, the bodily sample comprising at least one of blood, plasma, sera, saliva, mucous, synovial fluid, cerebrospinal fluid, urine, stool, cells, a cellular extract, a tissue sample, or a tissue biopsy.

6. The method of claim 1, the bodily sample comprising liver tissue, and the method measuring ethanol induced oxidative liver injury in a subject.

7. The method of claim 1, wherein the control level comprises a level of isolevuglandin and/or levuglandin ethanolamine phospholipid adducts in a normal or healthy subject or tissue.

8. The method of claim 1, wherein the control level comprises a previously measured level of isolevuglandin and/or levuglandin ethanolamine phospholipid adducts in the subject or tissue of the subject.

9. A method of measuring isolevuglandin and/or levuglandin ethanolamine phospholipid adducts associated with oxidative injury in a subject, the method comprising:
obtaining a bodily sample suspected of including isolevuglandin and/or levuglandin ethanolamine phospholipid adducts from a subject,
extracting lipids from said bodily sample,
selectively hydrolyzing isolevuglandin and/or levuglandin ethanolamine phospholipid adducts from the extracted sample with a phospholipase A2 (PLA2) enzyme to form isolevuglandin and/or levuglandin 2-lysoethanolamine phospholipid derivatives, and determining the amount of isolevuglandin and/or levuglandin 2-lysoethanolamine phospholipid derivatives by mass spectrometry, wherein the amount of isolevuglandin and/or levuglandin 2-lysoethanolamine phospholipid derivatives is determinative of the level of isolevuglandin and/or levuglandin ethanolamine phospholipid adducts in the sample and indicative of the level of oxidative injury in the subject, and wherein an increased level of isolevuglandin and/or levuglandin ethanolamine phospholipid adducts in the subject compared to a control level is indicative of an increased level of oxidative injury in the subject.

10. The method of claim 9, wherein isolevuglandin and/or levuglandin ethanolamine phospholipid adducts are extracted from the bodily sample in the presence of at least one of a chelating agent or antioxidant to inhibit oxidation of the bodily sample.

11. The method of claim 10, the chelating agent or antioxidant comprising at least one of ethylenediaminetetraacetic acid (EDTA) or butylated hydroxytoluene (BHT).

12. The method of claim 9, the bodily sample comprising at least one of blood, plasma, sera, saliva, mucous, synovial fluid, cerebrospinal fluid, urine, stool, cells, a cellular extract, a tissue sample, or a tissue biopsy.

13. The method of claim 9, the bodily sample comprising liver tissue, and the method measuring ethanol induced oxidative liver injury in a subject.

14. The method of claim 9, wherein the control level comprises a level of isolevuglandin and/or levuglandin ethanolamine phospholipid adducts in a normal or healthy subject or tissue.

15. The method of claim 9, wherein the control level comprises a previously measured level of isolevuglandin and/or levuglandin ethanolamine phospholipid adducts in the subject or tissue of the subject.

16. A method of measuring oxidative damage in a subject, the method comprising:

obtaining a bodily sample suspected of including isolevuglandin and/or levuglandin ethanolamine phospholipid adducts from a subject, extracting lipids from said bodily sample in the presence of chelating agent or antioxidant, selectively hydrolyzing isolevuglandin and/or levuglandin ethanolamine phospholipid adducts from the extracted sample with a phospholipase A2 (PLA2) enzyme to form isolevuglandin and/or levuglandin 2-lysoethanolamine phospholipid derivatives, and determining the amount of isolevuglandin and/or levuglandin 2-lysoethanolamine phospholipid derivatives by mass spectrometry, wherein the amount of isolevuglandin and/or levuglandin 2-lysoethanolamine phospholipid derivatives is determinative of the level of isolevuglandin and/or levuglandin ethanolamine phospholipid adducts in the sample and indicative of the level of oxidative damage in the subject, and wherein an increased level of isolevuglandin and/or levuglandin ethanolamine phospholipid adducts in the subject compared to a control level is indicative of an increased level of oxidative injury in the subject.

17. The method of claim 16, the chelating agent or antioxidant comprising at least one of ethylenediaminetetraacetic acid (EDTA) or butylated hydroxytoluene (BHT).

18. The method of claim 16, the bodily sample comprising at least one of blood, plasma, sera, saliva, mucous, synovial fluid, cerebrospinal fluid, urine, stool, cells, a cellular extract, a tissue sample, or a tissue biopsy.

19. The method of claim 16, the bodily sample comprising liver tissue, and the method measuring ethanol induced oxidative liver damage in the liver of the subject.

20. The method of claim 16, wherein the control level comprises a level of isolevuglandin and/or levuglandin ethanolamine phospholipid adducts in a normal or healthy subject or tissue.

21. The method of claim 16, wherein the control level comprises a previously measured level of isolevuglandin and/or levuglandin ethanolamine phospholipid adducts in the subject or tissue of the subject.

22. The method of claim 1, the isolevuglandin and/or levuglandin ethanolamine phospholipid adducts comprising isolevuglandin and/or levuglandin phosphatidylethanolamine adducts.

23. The method of claim 9, the isolevuglandin and/or levuglandin ethanolamine phospholipid adducts comprising isolevuglandin and/or levuglandin phosphatidylethanolamine adducts.

24. The method of claim 16, the isolevuglandin and/or levuglandin ethanolamine phospholipid adducts comprising isolevuglandin and/or levuglandin phosphatidylethanolamine adducts.

* * * * *